(12) United States Patent
Mu

(10) Patent No.: US 11,501,474 B2
(45) Date of Patent: Nov. 15, 2022

(54) COLLIMATORS FOR MEDICAL IMAGING SYSTEMS AND IMAGE RECONSTRUCTION METHODS THEREOF

(71) Applicant: Argospect Technologies Inc., Foster City, CA (US)

(72) Inventor: Zhiping Mu, Foster City, CA (US)

(73) Assignee: ARGOSPECT TECHNOLOGIES INC., Foster City, CA (US)

( * ) Notice: Subject to any disclaimer, the term of this patent is extended or adjusted under 35 U.S.C. 154(b) by 58 days.

(21) Appl. No.: 16/792,730

(22) Filed: Feb. 17, 2020

(65) Prior Publication Data

US 2020/0261034 A1    Aug. 20, 2020

Related U.S. Application Data

(60) Provisional application No. 62/807,106, filed on Feb. 18, 2019.

(51) Int. Cl.
*G21K 1/02* (2006.01)
*G06T 11/00* (2006.01)
(Continued)

(52) U.S. Cl.
CPC ........... *G06T 11/006* (2013.01); *A61B 6/032* (2013.01); *A61B 6/06* (2013.01); *A61B 6/4064* (2013.01); *A61B 6/4291* (2013.01); *A61B 6/486* (2013.01); *A61B 6/5205* (2013.01); *A61B 6/5235* (2013.01); *G06T 5/006* (2013.01);
(Continued)

(58) Field of Classification Search
CPC .......... A61B 6/032; A61B 6/037; A61B 6/06; A61B 6/4064; A61B 6/4291; A61B 6/486; A61B 6/5205; A61B 6/5235; A61B 6/4035; A61B 6/4057; A61B 6/4233; A61B 6/4258; A61B 6/4266; A61B 6/4447; A61B 6/461; A61B 6/502; A61B 6/5211; A61B 6/548; A61B 6/583; G01T 1/1647; G01T 1/295; G01T 1/2985; G01T 1/2921; G06T 11/006; G06T 2207/10081; G06T 2210/41; G06T 2211/424; G06T 5/006; G06T 7/0012; G21K 1/025; G21K 1/02; G01N 23/20; G01N 23/207; G01N 23/20066;
(Continued)

(56) References Cited

U.S. PATENT DOCUMENTS 6,580,939 B1    6/2003  Chaney et al.
9,057,684 B2 *  6/2015  Williams .............. G01T 1/2921
(Continued)

OTHER PUBLICATIONS

International Searching Authority, International Search Report, PCT/US20/18663, dated May 18, 2020, 10 pages, Alexandria, Virginia.
(Continued)

*Primary Examiner* — Irakli Kiknadze
(74) *Attorney, Agent, or Firm* — Haynes and Boone, LLP

(57) ABSTRACT

According to various embodiments, the present disclosure provides a collimator for medical imaging. The collimator includes a perforated plate with a top surface and a bottom surface and holes distributed on the perforated plate. The holes are arranged in a plurality of groups. The plurality of groups forms a first coded aperture pattern and the holes in each of the plurality of groups form a second coded aperture pattern.

20 Claims, 12 Drawing Sheets

(51) Int. Cl.
*G06T 5/00* (2006.01)
*G06T 7/00* (2017.01)
*A61B 6/03* (2006.01)
*A61B 6/00* (2006.01)
*A61B 6/06* (2006.01)

(52) U.S. Cl.
CPC ............ *G06T 7/0012* (2013.01); *A61B 6/037* (2013.01); *G06T 2207/10081* (2013.01); *G06T 2210/41* (2013.01); *G06T 2211/424* (2013.01)

(58) Field of Classification Search
CPC ... H04N 5/357; H04N 9/04557; H04N 5/3572
USPC .................................................. 378/147–153
See application file for complete search history.

(56) References Cited

U.S. PATENT DOCUMENTS

| | | | | |
|---|---|---|---|---|
| 9,250,200 | B1* | 2/2016 | Grubsky | G01N 23/046 |
| 2008/0095298 | A1* | 4/2008 | Shefsky | G01T 1/295 |
| | | | | 250/358.1 |
| 2008/0230707 | A1 | 9/2008 | Idoine | |
| 2010/0067766 | A1 | 3/2010 | Vija | |
| 2011/0190616 | A1 | 8/2011 | Marwala et al. | |
| 2012/0027173 | A1* | 2/2012 | Duerr | G01N 23/04 |
| | | | | 378/62 |
| 2012/0305812 | A1 | 12/2012 | Bowen et al. | |
| 2013/0038766 | A1* | 2/2013 | Perlman | H04N 5/357 |
| | | | | 257/E31.127 |
| 2013/0299705 | A1 | 11/2013 | Mu | |
| 2015/0146848 | A1* | 5/2015 | Gupta | G01V 5/0016 |
| | | | | 378/57 |
| 2017/0098316 | A1 | 4/2017 | Ma et al. | |

OTHER PUBLICATIONS

European Patent Office: "Extended European Search Report", Application No. 20758637.1-1210/3927239 PCT/US2020018663, dated Apr. 7, 2022, 9 pages.

Hong Stephen Baoming: "Three-Dimensional reconstruction methods in near-field coded aperture for spect imaging system" In: "Computer vision in medical imaging", Jan. 2014 (Jan. 2014), World Scientific, XP055905086, ISBN: 978-981-4460-94-I pp. 175-188, DOI: 10.1142/9789814460941_0010.

Zhiping Mu et al: "Aperture Collimation Correction and Maximum-Likelihood Image Reconstruction for Near-Field Coded Aperture Imaging of Single Photon Emision Computerized Tomography", IEEE Transactions On Medical Imaging, IEEE, USA, vol. 25, No. 6, Jun. 2006 (Jun. 2006), pp. 701-711, XP001545905,ISSN: 0278-0062, DOI:10.1109/TMI.2006.873298.

* cited by examiner

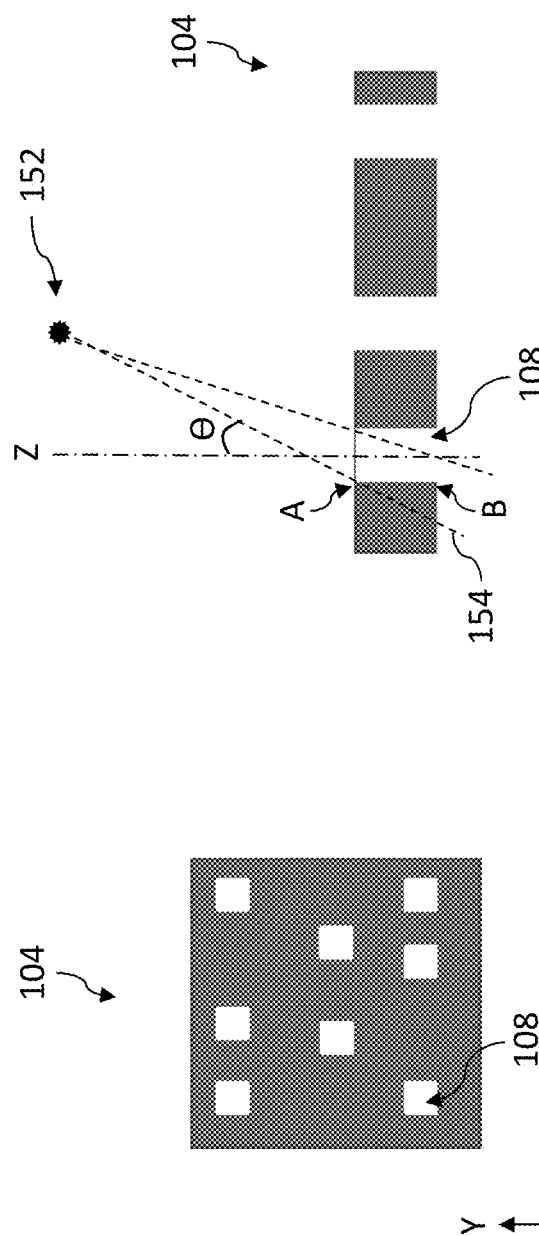

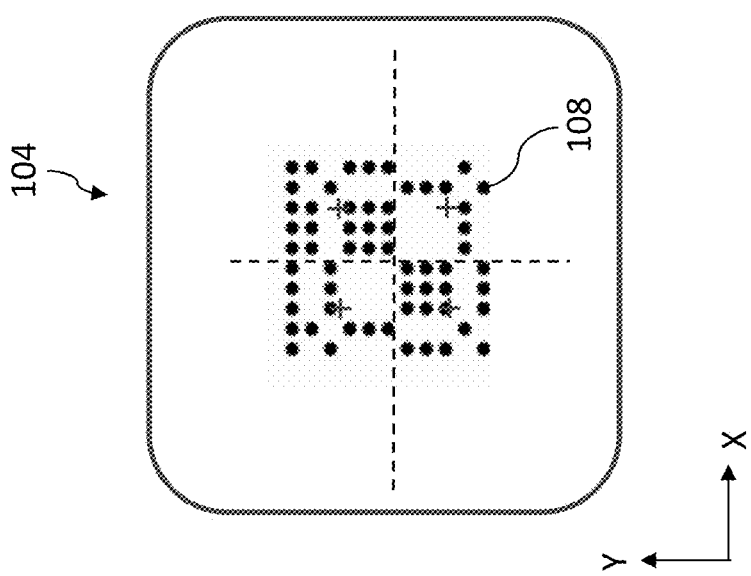

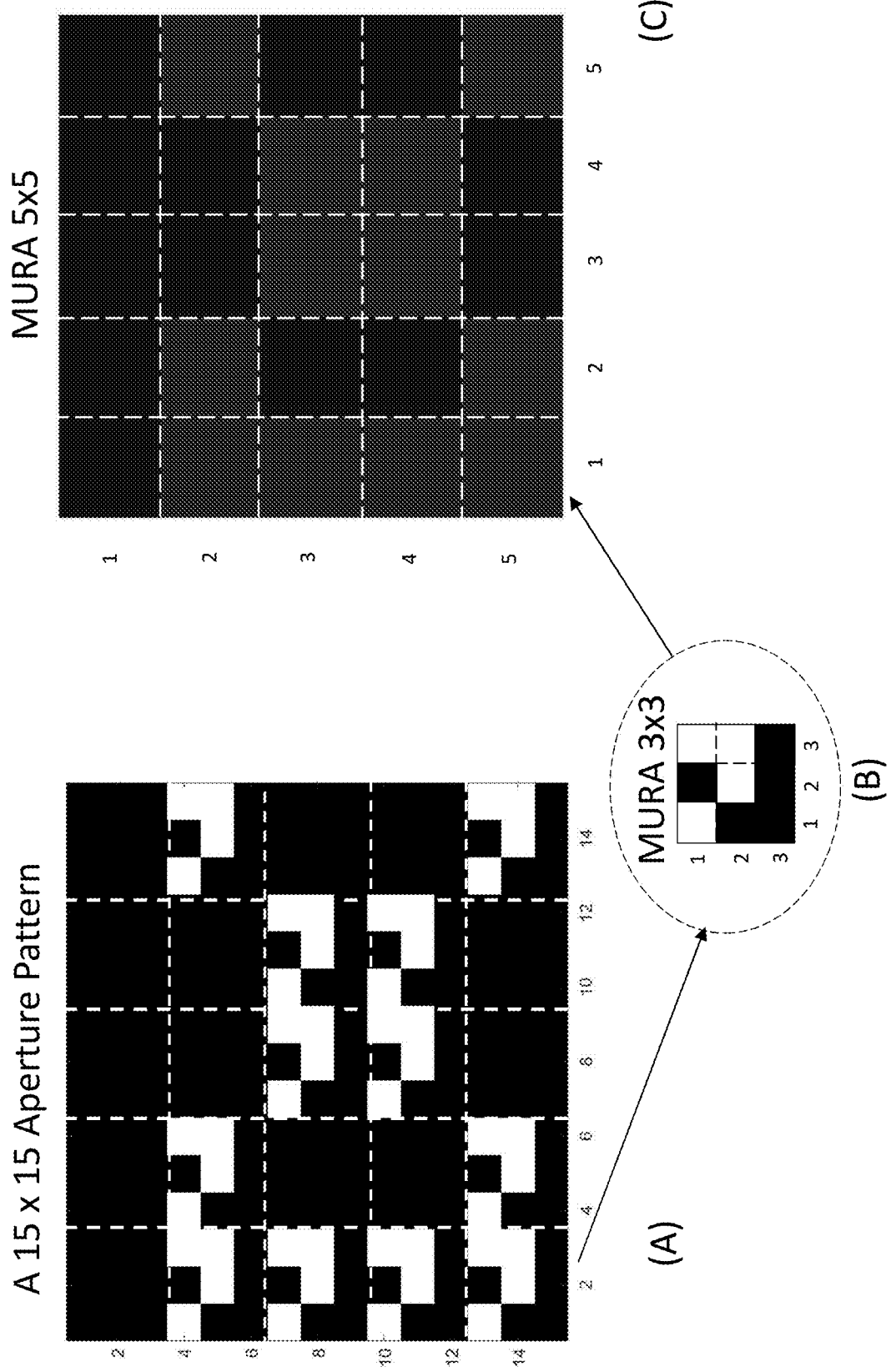
FIGS. 11A, B, C

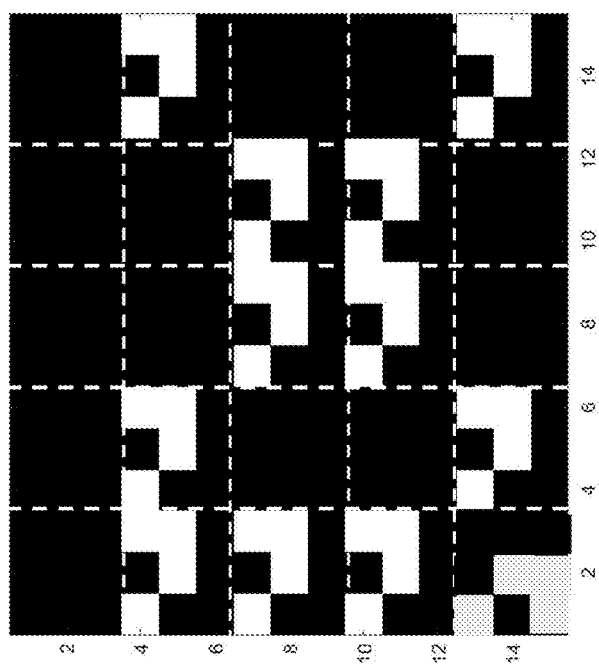
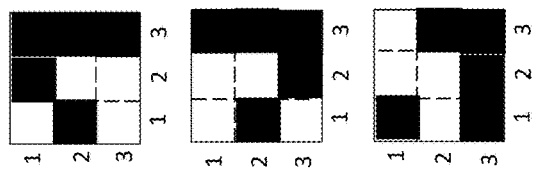
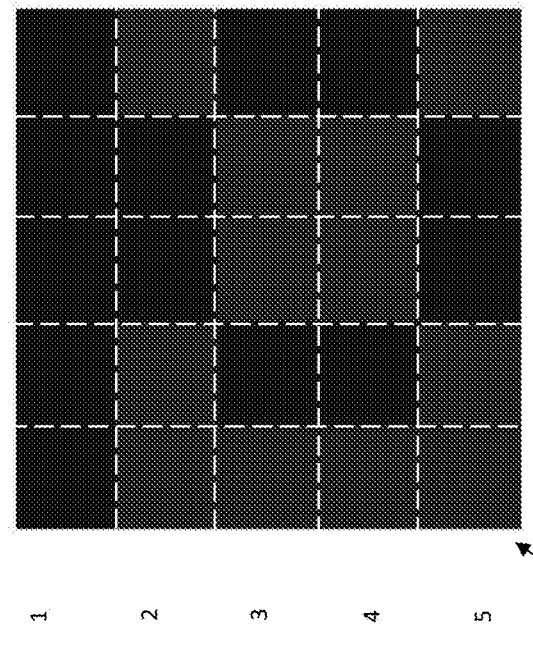
FIGS. 12A, B, C

COLLIMATORS FOR MEDICAL IMAGING SYSTEMS AND IMAGE RECONSTRUCTION METHODS THEREOF

PRIORITY

This application claims priority to U.S. Provisional Patent Application Ser. No. 62/807,106 filed on Feb. 18, 2019, the entire disclosure of which is incorporated herein by reference.

BACKGROUND

In molecular medical imaging, sometimes known as nuclear medicine, images representing radiopharmaceutical distributions may be generated for medical diagnosis. Prior to imaging, radiopharmaceuticals are injected into an imaging subject such as a patient. The radiopharmaceuticals emit radioactive photons, which can penetrate through the body to be detected by a photon detector. Based on information from the received photons, the photon detector may then determine the distribution of the radiopharmaceuticals inside the patient. Their distribution represents the physiological function of the patient, and therefore images of their distribution provide valuable clinical information for diagnosis of a variety of diseases and conditions such as those in cardiology, oncology, neurology, etc.

A collimator is a device that guides photon path. In molecular imaging, photons may originate from unknown locations inside a subject, unlike in X-ray or CT where photons are emitted from a known source (or sources) position. Without collimators, photons from all directions may be recorded by gamma detectors, and image reconstruction may become difficult. Therefore, collimators are employed to guide possible photon paths so that images can be reconstructed, similar to the role of lens in a photography camera. Although existing collimator and detector imaging systems have been generally adequate for their intended purposes, they have not been entirely satisfactory in all respects. For example, existing imaging systems are often limited by background noise and nonuniformity artifacts. Therefore, improvement on image reconstruction methods is desired to increase imaging sensitivity or resolution for collimator and detector based medical imaging systems.

SUMMARY

According to various embodiments, the present disclosure provide a method of imaging reconstruction, including providing a target object, a detector, and a mask disposed between the target object and the detector; acquiring a measured image of the target object by the detector; providing an estimated image of the target object; partitioning the mask into multiple regions; for each of the regions, deriving a forward projection from the estimated image of the target object and the respective region, thereby acquiring multiple forward projections; comparing the measured image of the target object with the forward projections; and updating the estimated image of the target object based on a result of the comparing. In some embodiments, the method further includes repeating the steps of deriving, comparing, and updating. In some embodiments, the method further includes on condition that a difference of the estimated images of the target object in consecutive two steps is less than a predetermined threshold, storing one of the estimated images of the target object as a reconstructed image of the target object. In some embodiments, the method further includes on condition that the step of updating the estimated image of the target object is repeated for a predetermined number of times, storing the estimated image of the target object as a reconstructed image of the target object. In some embodiments, the method further includes repeating the steps of partitioning, deriving, comparing, and updating, wherein a number of the regions increases during the repeating of the steps. In some embodiments, the deriving of the forward projection includes a convolution operation. In some embodiments, the deriving of the forward projection includes for each of the regions calculating a respective angular effect correction factor. In some embodiments, the angular effect correction factor includes a $\cos^3(\theta)$ term, $\theta$ being an incident angle. In some embodiments, the mask has multiple through holes, and wherein each of the regions has at least one through hole. In some embodiments, the mask has at least two regions having different numbers of through holes. In some embodiments, each of the regions has a convex shape. In some embodiments, updating the estimated image includes for each of the regions calculating a backward projection based on applying a respective forward projection to a correlation operation.

According to various embodiments, the present disclosure also provides a method of imaging processing, including providing a target object and a mask partially blocking a radiation from the target object; providing an estimated image of the target object; partitioning the mask into multiple regions; for each of the regions, deriving a forward projection from the estimated image of the target object and the respective region, thereby acquiring multiple forward projections. wherein the deriving of the forward projection includes for each of the regions calculating a respective angular effect correction factor. In some embodiments, the angular effect correction factor includes a $\cos^3(\theta)$ term, $\theta$ being an incident angle. In some embodiments, the method further includes acquiring a measured image of the target object by a detector; comparing the measured image of the target object with the forward projections; and updating the estimated image of the target object based on a result of the comparing.

According to various embodiments, the present disclosure also provides a medical imaging system, including a collimator configured to filter radiation emitted from a target object; a detector configured to acquire a measured image of the target object by detecting the radiation that has passed through the collimator; and a controller operable to execute computer-readable codes to perform following operations: receiving the measured image from the detector; providing an estimated image of the target object; partitioning the collimator into multiple regions; for each of the regions, deriving a forward projection, thereby acquiring multiple forward projections; and updating the estimated image based on a result of comparing the measured image and the forward projections. In some embodiments, the initial estimated image is acquired from a CT scan. In some embodiments, steps of deriving the forward projection and updating the estimated image are part of an iteration operation. In some embodiments, the step of partitioning the collimator is also part of the iteration operation, and wherein a number of the regions increases during the iteration operation. In some embodiments, for each of the regions, there is one or more through holes forming a coded aperture pattern.

According to various embodiments, the present disclosure also provides a collimating apparatus for medical imaging, including a perforated plate with a top surface and a bottom surface; and a plurality of holes, wherein each of the plurality of holes extends from the top surface to the bottom surface, wherein: the plurality of holes is grouped into two or more regions of the perforated plate; and each of the two or more regions includes a coded aperture pattern formed by a portion of the plurality of holes. In some embodiments, the coded aperture pattern is one of a URA array, a MURA array, a random array, and a pseudo random array. In some embodiments, the coded aperture pattern in each of the two or more regions is different from each other.

BRIEF DESCRIPTION OF THE DRAWINGS

The present disclosure is best understood from the following detailed description when read with the accompanying figures. It is emphasized that, in accordance with the standard practice in the industry, various features are not drawn to scale and are used for illustration purposes only. In fact, the dimensions of the various features may be arbitrarily increased or reduced for clarity of discussion.

FIGS. 2A and 2B are schematic top and cross-sectional views, respectively, of an exemplary collimator according to various aspects of the present disclosure.

FIGS. 3A and 3B are a schematic top view and corresponding matrix of an exemplary partitioned collimator according to various aspects of the present disclosure.

FIGS. 11A, 11B, 11C, 12A, 12B, and 12C are exemplary collimator designs that provide multi-levels of resolutions.

DETAILED DESCRIPTION

Figure 1:
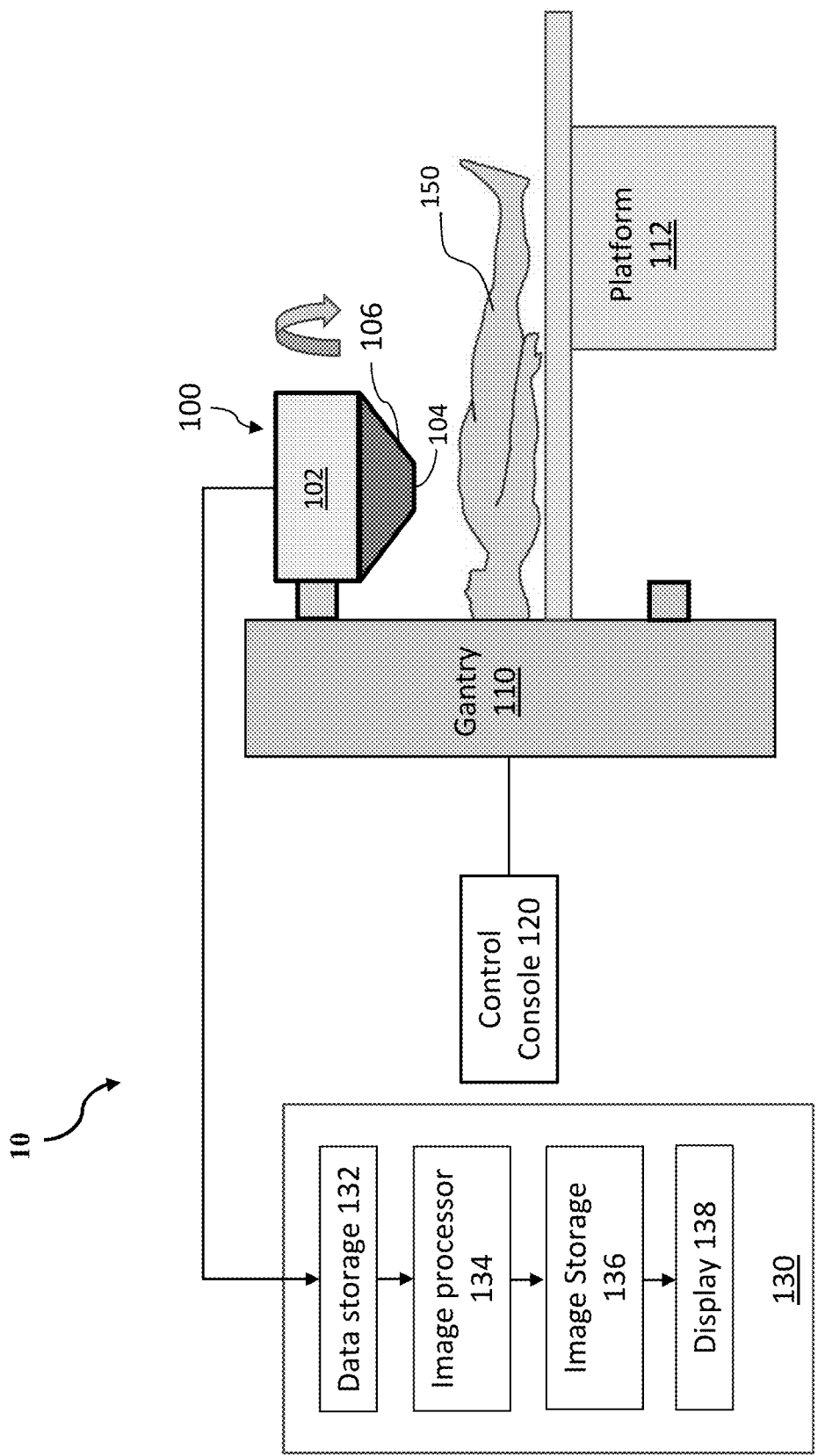
FIG. 1 is a schematic diagram of an exemplary nuclear imaging system according to various aspects of the present disclosure.

The following disclosure provides many different embodiments, or examples, for implementing different features of the disclosure. Specific examples of components and arrangements are described below to simplify the present disclosure. These are, of course, merely examples and are not intended to be limiting. Any alterations and further modifications to the described devices, systems, methods, and any further application of the principles of the present disclosure are fully contemplated as would normally occur to one having ordinary skill in the art to which the disclosure relates. For example, the features, components, and/or steps described with respect to one embodiment may be combined with the features, components, and/or steps described with respect to other embodiments of the present disclosure to form yet another embodiment of a device, system, or method according to the present disclosure even though such a combination is not explicitly shown. In addition, the present disclosure may repeat reference numerals and/or letters in the various examples. This repetition is for simplicity and clarity and does not in itself dictate a relationship between the various embodiments and/or configurations discussed.

Moreover, a feature on, connected to, and/or coupled to another feature in the present disclosure that follows may include embodiments in which the features are in direct contact, and may also include embodiments in which additional features may interpose the features, such that the features may not be in direct contact. In addition, spatially relative terms, for example, "lower," "upper," "horizontal," "vertical," "above," "over," "below," "beneath," "up," "down," "top," "bottom," etc., as well as derivatives thereof (e.g., "horizontally," "downwardly," "upwardly," etc.) are used for ease of the present disclosure of one features relationship to another feature. The spatially relative terms are intended to cover different orientations of the device including the features. Still further, when a number or a range of numbers is described with "about," "approximate," and the like, the term is intended to encompass numbers that are within a reasonable range including the number described, such as within +/−10% of the number described or other values as understood by person skilled in the art. For example, the term "about 5 mm" encompasses the dimension range from 4.5 mm to 5.5 mm.

The present disclosure is generally related to the field of medical imaging, and more particularly to an imaging reconstruction method to collimator and detector based medical imaging systems, such as to single photon emission computerized tomography (SPECT) or positron emission tomography (PET) based on near-field coded aperture collimation and maximum likelihood estimation in some embodiments.

Prior to taking molecular medical images, a radiopharmaceutical is usually taken orally or injected into the patient. The radiopharmaceutical undergoes nuclear decay, emitting, either directly or indirectly through annihilation, gamma photons at certain rates and with characteristic energies. One or more detector unit are placed around the patient or object to record or monitor emissions. In many cases, for convenience of manufacturing and data processing, the detectors are organized in planar shape, therefore acquire data in 2D matrix format, which are often referred to as projections. Based on the recorded information including position, energy and counts of such detected events, an image of the radiopharmaceutical distribution can be reconstructed to study the function of certain body parts.

FIG. 1 illustrates an exemplary molecular or nuclear imaging system 10, which may be used to medically examine or treat a subject such as a patient. In one embodiment, imaging system 10 is a SPECT imaging system. Alternatively, imaging system 10 can be other molecular or nuclear imaging systems, such as a PET imaging system. For the sake of simplicity, a SPECT imaging system will be illustrated as an example to demonstrate image reconstruction methods. However, a person in the pertinent field will understand the proposed image reconstruction methods are not limited to a SPECT imaging system, but can be applied to other suitable imaging systems, such as a PET imaging system. Imaging system 10 includes an imaging apparatus 100, a gantry 110, a platform 112, a control console 120, and a computer system 130. In the illustrated embodiment, computer system 130 includes a data storage unit 132, an image processor 134, an image storage unit 136, and a display 138. Imaging apparatus 100 is mounted on gantry 110, which may move, rotate, and acquire data. Patient 150 is placed on platform 112 (e.g., a couch) for examination or treatment by the imaging apparatus 100. In some embodiments, imaging apparatus 100 is coupled to gantry 110 through movable parts so that they may move (e.g., rotate) on gantry 110.

Imaging apparatus 100 detects and records radiation emitted from patient 150 and transfers recorded information to data storage unit 132. Then, image processor 134 may use the recorded information to reconstruct volumetric images representing radiopharmaceutical distributions within patient 150. The reconstructed images are stored in image storage unit 136, which can be manipulated and displayed on display 138 for viewing. Control console 120 may be used by an operator or technician to control imaging apparatus 100 in acquiring data. In some embodiments, control console 120, data storage unit 132, image processor 134, image storage unit 136, and display 138 are integrated in a computer system 130. In some embodiments, one or more computer components (such as control console 120, data storage unit 132, image processor 134, image storage unit 136, and display 138) can be partially or entirely located at a remote location (e.g., on the cloud). In some embodiments, one of more of these components may exist locally or remotely.

Imaging apparatus 100 includes detector 102 and collimator (or collimators) 104. In some embodiments, detector 102 is a semiconductor detector, such as one based on cadmium telluride (CdTe), cadmium zinc telluride (CZT), or high purity germanium (HPGe). In some embodiments, detector 102 is a scintillator (such as sodium iodide (NaI) or caesium iodide (CsI) based) detector. In some other embodiments, detector 102 may also be a scintillator coupled with compact photo multiplier tubes (PMTs), silicon photomultiplier tubes (SiPMT), or avalanche photodiodes. Collimator 104 includes one or more openings, such as through holes. Depending on number and geometrical placement of through holes, collimator 104 may be a single-pinhole, multi-pinhole, coded aperture, or extended coded aperture (also known as spread field imaging, SFI) collimator, or other suitable types of collimator. Depending on profiles of through holes, collimator 104 may be a parallel-hole, fan-beam, or cone-beam collimator, or other suitable types of collimator.

One or more radiopharmaceuticals orally taken or injected into patient 150 undergo nuclear decay and may emit, either directly or indirectly through annihilation, radiation (e.g., gamma photons) at certain rates and with characteristic energies. Detector 102 is placed near patient 150 to record or monitor emissions. Based on recorded information such as position, energy, and counts of such detected events, an image of radiopharmaceutical distribution may be reconstructed to study the status or function of certain body parts on patient 150. In SPECT imaging, collimator 104 is placed between detector 102 and an imaging object, the openings on the collimators determining the directions and angular span from which radiation can pass through to reach certain position on the detector.

In various embodiments, collimators are essentially perforated plates usually made of heavy metal such as lead and tungsten. In some embodiments, the collimator is made of planar plates, usually placed in parallel to the planar detector surface. The thickness of the plate, depending on the energy of photons it is designed to imaging, is large enough to stop the majority of the radiation so that the photons primarily pass through the small pinholes on the plate. For example, for the commonly used isotope, Technetium-99m (99mTc), emitting gamma rays with energy around 140 keV, a 3 mm thickness is usually enough for a plate made of lead, and about 2 mm for tungsten. The thickness needs to be greater to image higher energy gamma rays. These collimators need to be placed at certain distance from the detector to allow photons coming from the design field-of-view (FOV) passing the pinhole(s) to spread across the detector surface. A gap between a collimator and a detector in this scenario is usually greater than 3 cm.

Imaging apparatus 100 may include other necessary parts for an imaging gantry such as connectors that couple parts together (e.g., connecting detector 102 and collimator 104 together), motors that cause parts to move, photon shielding components, a housing component that contains other parts, etc. For example, a coupling and shielding component 106 may connect detector 102 and collimator 104 such that both move (e.g., rotate) together, and prevent radiation (photons) from reaching detector 102 through paths other than collimator 104. In other embodiments, detector 102 and collimator 104 may move individually with respect to each other.

FIGS. 2A and 2B illustrate a top view and a cross-sectional side view of an exemplary collimator 104. Collimator 104 is configured to filter radiation by blocking certain photons and passing through other photons. Collimator 104 is made of radiation (e.g., photons) absorbing heavy metal(s), such as lead and/or tungsten. Collimator 104 has openings 108 built therein to allow some photons to pass through and reach detector 102 (FIG. 1). It should be understood that radiation or photon blocking or absorption by a collimator does not require blocking of 100% of photons because a small percentage of photons (e.g., 5% or less) may still penetrate through the full thickness of the radiation absorbing material. The number of escaping photons may decrease exponentially with the thickness of a collimator. In other words, blocking (or other similar terms) means that substantially all of the photons (e.g., 95% or more, or 99% or more) are absorbed by the radiation absorbing material.

Openings 108 may be through holes that extend from a top surface of the collimator to a bottom surface of the collimator. Alternatively, openings 108 may be substantially through the collimator—such as being recesses from a top surface of the collimator with a depth of over 98% of a thickness of the collimator. Openings 108 may also be called through holes, tunnels, apertures, or pass-through features—may have any suitable shape, size, number, and/or distribution within their respective collimators. In some embodiments, openings 108 may include parallel holes, fan beams, cone beams, slit-slat, pinholes, multi-pinholes, coded aperture, any other suitably shaped openings, or combinations thereof. In some embodiments, collimator 108 is placed close (e.g., 2 cm or less) to patient 150. Thus, collimator 108 may use parallel holes or fan-beams (converging or diverging) since such features do not need significant separation from patient 150. In some embodiments, openings 108 may be slanted, converging, or diverging and may form fan beams or cone beams, etc. In an example, openings 108 include a plurality of pinholes, where the number of pinholes may be greater than 11, greater than 23, or greater than 59, or greater than 100. Openings 108 may form a coded aperture pattern, for example, an MURA (modified uniformly redundant array) of sizes 5, 7, 11, and 13 comprise 12, 24, 60, and 84 holes, respectively. A higher number of pinholes helps improve imaging sensitivity. Further, openings 108 may be single pinhole, multi-pinhole, multiple pinhole modules (including spread field imaging (SFI) or coded aperture).

As shown in FIG. 2B, a radiation source (e.g., from a part of patient 150) 152 emits photons from above collimator 104. Photons hit a top surface of collimator 104 will be blocked. Photons passing through a top side (the side facing the radiation source) of opening 108 may still be blocked by its side walls. An incident path 154 of a photon hitting an edge point A of the top opening of opening 108 forms an angle θ with respect to vertical direction Z that is the normal of the top surface of collimator 104. The angel θ is referred to as an incident angle. When incident angle θ is not equal to 0 degree (θ≠0), the radiation source 152 is termed an off-center source. The incident angle θ is considered substantially the same when the incident path 154 is measured from another point of opening 108, such as measured from an edge point B at the bottom side of opening 108, or any point between edge points A and B, or a point in close proximity to opening 108 if the thickness and opening are substantially smaller than the distance between the source 152 and the opening 108.

If a photon travels towards collimator 104 along an incident path with an angle larger than the incident angle θ, the photon would be absorbed by collimator 104 (note there are occasions where the photon cuts through a portion of collimator 104 adjacent the opening (e.g., a thin area on the sidewall of the opening)). In some embodiments, the incident angle θ ranges from 0° to about 2° or from 0° to about 10°. In an example, a LEHR (low energy high resolution) collimator has an opening diameter of about 1.11 mm and a length of about 24.04 mm, with an acceptable incident angle range of 0° to about 2.64°. In another example, a GAP (general all purpose) collimator has an opening diameter of about 1.40 mm and a length of about 25.4 mm, with an acceptable incident angle range of 0° to about 3.15°. In yet another example, a LEHS (low energy high sensitivity) collimator has an opening diameter of about 2.54 mm, a length of about 24.04 mm, with an acceptable incident angle range of 0° to about 6.03°. In some other examples, acceptable incident angle ranges from 0° to about 15°, or 0° to about to 75°. For example, an opening with a diameter of about 1.0 mm and a length of about 3.0 mm has an acceptable incident angle of about 18.43°, and an opening with a diameter of about 3.0 mm and a length of about 1.5 mm has an acceptable incident angle of about 63.43°.

Between radiation source 152 and detector 102, collimator 104 functions as a mask. Each radiation source 152 from patient 150 projects onto detector 102 a shadow of the mask weighted by the intensity of radiation source 152. The location of the shadow depends on the direction of the incident photons from radiation source 152. As a result, a raw image acquired by detector 102 is a summation of the shadows cast by all of the radiation source 152 within field-of-view (FOV) of the collimator 104. Image reconstruction is thus to construct an estimated image of radiation sources 152 (referred to as object image) from the raw image(s) acquired by detector 102 (referred to as measured image). Mathematically, an imaging system can be approximately represented by a simplified model without considering noise as $$p=f*h \tag{1}$$

where * represents the convolution operator, p is the measured image, f is the object image, and h represents the coded pattern formed in the collimator. In other words, h is a matrix, representing the coded mask shadow. In some embodiments, h is a matrix of "0"s and "1"s, where each element corresponds to a grid position on the collimator, 1 represents an opening (e.g., a pinhole) at that position, and 0 represents otherwise. This matrix can be magnified to represent the magnifying effect of the mask shadow projected by a source on the detector, and interpolation may be used to calculate the matrix element values.

Image reconstruction can be considered as a decoding procedure. The object image f can be estimated by decoding, i.e., correlating the measured image p with a decoding mask pattern g. This decoding procedure can be represented as $$\hat{f}=p\otimes g=f*(h\otimes g) \tag{2}$$

where $\hat{f}$ denotes an estimation of the object image, ⊗ represents the correlation operator, and g is the decoding mask satisfying $$h\otimes g=\delta \tag{3}$$

From a two-dimensional (2D) point of view, measured image p can be divided into a plurality of smaller regions, representing by $p_i$. For example, if based on x- and y-coordinates of the plane a collimator resides, a region can be denoted as $p_{xy}$. When a planar detector is used, the X- and Y-axes are usually parallel to the detector surface, and Z-axis is perpendicular to the detector surface. Similarly, object image f can be divided into a plurality of smaller regions, representing by $f_j$ or as $f_{xy}$ on an X-Y plane. In one embodiment, an image reconstruction method is called a Maximum Likelihood Expectation and Maximization (MLEM) method. The MLEM method is derived from the Poisson noise model and maximization of $P(\hat{f}|p)$, the probability of an estimated object image $\hat{f}$ given the measured image p. The MLEM method estimates object images using $$\hat{f}_j^{(k+1)} = \frac{\hat{f}_j^{(k)}}{\sum_{i=1}^{I} K_{ij}} \sum_{i=1}^{I} \frac{p_i K_{ij}}{\sum_{j=1}^{J} K_{ij}\hat{f}_j^{(k)}} \tag{4}$$

where $\hat{f}_j^{(k+1)}$ is the (k+1)th estimate of the jth element of f, the object image; $p_i$ is the ith element of the measured image, and $K_{ij}$ is the transition matrix representing the probability of photon emitted from $j_{th}$, element of the object being detected by the ith element of the detector. The values of Kij can be determined by measurement, simulation, or modeling of the collimator. Let $p_r$ be the denominator inside the second summation, $p_r=\Sigma_{j=1}^{J}K_{ij}\hat{f}^{(k)}$, representing an expectation of measured image based on the kth estimated object image, $\hat{f}^{(k)}$. This step is often referred to as the forward projection.

In some cases, such as when a coded aperture mask is used as a collimator, the projection image can be corrected for the angular effect (including $\cos^3(\theta)$ term and aperture collimation effect term) prior to the MLEM iterative deconvolution process. By doing so, the imaging model becomes a convolution process and equation (4) can be further written as $$\hat{f}^{(k+1)} = \hat{f}^{(k)} \times \left( h \otimes \frac{p_c}{\hat{f}^{(k)}*h} \right) \tag{5}$$

whereas discussed above, h is a coded aperture mask shadow, and $p_c$ is a measured image after correction for angular and collimation effects. Specifically, $p_c$=p/Cc, where Cc is the angular effect correction factor (e.g., in a matrix form) that is a smooth function that accounts for one or more factors including $\cos^3(\theta)$ term and aperture collimation effect term. Here the angle θ is between an incident path of a photon passing through a point on collimator, usually the center of the collimator, hitting a pixel on detector with respect to vertical direction Z that is the normal of the top surface of collimator. And * and ⊗ represent convolution and correlation operations, respectively. Equation (5)

includes two major procedures: forward projection and backward projection. The convolution represents the forward projection step using current estimation of $\hat{f}^{(k)}$. The correlation with the Cc correction resulting from the division step of $p_c$ represents the backward projection step.

Equation (5) is suitable for a thin imaging object whose thickness is much smaller than the distance between the subject and a collimator such as collimator 122. For thicker objects, a three-dimensional (3D) method is used. For example, an object image at distance z (measured from the plane where the detector resides to the object) can be estimated using the following equation:

$$\hat{f}^{(K+1)}(Z) = \frac{\hat{f}^{(K)}(z)}{\sum_{x,y} h(z)} \left[ h(z) \otimes \frac{p_c}{\sum_z \hat{f}^{(K)}(z) * h(z)} \right] \quad (5\text{-}1)$$

A slightly different formula can be used to estimate the subject as well:

$$\hat{f}^{(K+1)}(z) = \frac{\hat{f}^{(K)}(z)}{\sum_{x,y} h(z)} \left[ h(z) \otimes \frac{p_c - \sum_{z \neq z'} \hat{f}^{(K)}(z') * h(z')}{\hat{f}^{(K)}(z) * h(z)} \right] \quad (5\text{-}2)$$

where $\hat{f}^{(K)}(z)$ is an estimation of the object at slice z after k iterations, and h(z) is the coded aperture mask shadow corresponding to z. The process expressed in equation (5-2) differs from the conventional MLEM deconvolution in that the expected contribution from the "out-of-focus" slices (z'≠z) is subtracted from the measured projection, and the correction ratio in the division step is calculated only for the "in-focus" slice (z'=z). More specifically, the correction ratio is computed only from the estimation errors in the in-focus slice. Hence, the algorithm is expected to converge faster. Further regarding distance z in 3D imaging, the partition of the object along Z-axis (perpendicular to the detector surface) may be equally spaced. Alternatively, the partition of object along Z-axis may be unevenly spaced (e.g., of variable distances).

In one embodiment, an image reconstruction method may divide object image into smaller regions. For example, an object plane at height z may be divided into n×n small regions, $f_i(z)$, i=1, . . . , $n^2$. For the ith region, a center angular effect correction factor $C_{Ci}$ for that region was computed by taking the center of the region as the collimation center. Then, in the forward projection step, the contribution of the current estimated image plane to the projection, $p_r(z)$, was calculated. More specifically, the $\hat{f}^{(K)}(z)*h(z)$ originally formulated in equation (5-2) is computed as:

$$p_r(Z) = \sum_{i=1}^{n^2} [\hat{f}_i^{(K)}(z) * h(z)] \times C_{Ci} \quad (6)$$

where $C_{Ci}$ is the angular effect correction factor for the ith region, $C_{ci} = C_c(x-x_{ci}, y-y_{ci})$, and $x_{ci}$, $y_{ci}$ are the x- and y-coordinates of a point in the ith region, usually the center of ith region of $\hat{f}^{(K)}(z)$. Note that all variables in equation (6) have x,y as parameters which are ignored for simplicity. Then the object image can be estimated using the following equation:

$$\hat{f}^{(K+1)}(z) = \frac{\hat{f}^{(K)}(z)}{\sum_{x,y} h(z)} \left[ h(z) \otimes \frac{p - \sum_{z \neq z'} p_r(z')}{p_r(z)} \right] \quad (6\text{-}1)$$

A slightly different formula can be used to estimate the object as well:

$$\hat{f}^{(K+1)}(z) = \frac{\hat{f}^{(K)}(z)}{\sum_{x,y} h(z)} \left[ h(z) \otimes \frac{p}{\sum_z p_r(z)} \right] \quad (6\text{-}2)$$

Note that in both equations (6-1) and (6-2), the original measured image, p, is used instead of $p_c$ as in equation (5).

The collimator matrix h described above assumes that recorded signal in p reflects only photons that can only pass through the openings on the collimator. In reality, signals from other channel exist. For example, photons can penetrate the metal plate at a rather low but greater than zero rate. For instance, with a 1 mm thick plate made of tungsten, less than 3% of photons with 140 keV energy can pass through. And there are random thermal or electrical events on the detector that contribute to the signal such as dark current. Therefore, a thorough computation of $p_r$ would include computation of signals going through channels other than the holes. Nevertheless, signals from photons passing through holes represent significant portion of the total signal and are a major component of interest, and steps can be taken to minimize the signals from other channels, such as increase plate thickness to reduce penetration.

The equations (5) and (6) described above are more accurate under a small mask assumption, which means detector size is much larger than a coded aperture mask size. However, in many situations, a larger mask is used to increase detection sensitivity. Therefore, a small mask assumption does not always hold, resulting in degradation in the image reconstruction.

To mitigate this issue and still approximate a small mask assumption, an image reconstruction method can be further improved by partitioning the mask, optionally represented by collimator matrix h, into small regions, such that each region is small enough to satisfy the small mask approximation. Thereafter, forward projection through each individual collimator region is calculated. Center angular correction for that collimator region may also be applied to each forward projection for adjustment. The forward projection through each individual region is then summed into an overall forward projection. For example, a collimator may be divided into n small regions, $h_i(z)$, i=1, . . . , n; for each region, a center angular effect correction factor $C_{Ci}$ suitable for that region was computed, optionally by taking the center of the region as the collimation center (Hereby the angle θ is between an incident path of a photon passing through a point in this collimator region, usually the center point of this region, hitting a pixel on detector with respect to vertical direction Z that is the normal of the top surface of collimator); then, in the forward projection step, the contribution of the current estimated image plane to the projection was calculated as $p_r(z)$. More specifically, the $f^{(K)}(z)*h(z)$ originally formulated in equation (6) is computed as:

$$p_r(Z) = \sum_{i=1}^{n} [\hat{f}^{(K)}(z) * h_i(z)] \times C_{Ci} \quad (7)$$

where $[\hat{f}^{(K)}(z) * h_i(z)]$ is the forward projection of the ith region of the collimator, $C_{ci}$ is the angular effect correction factor for the ith region of the collimator, and $p_r(z)$ is overall forward projection of image $\hat{f}^{(K)}(z)$. In one example, if all openings of the collimator are of the same size and shape, then $C_{Ci} = C_C(x-x_{ci}, y-y_{ci})$, which is the same function Cc shifted by various ($x_{ci}$, $y_{ci}$) values, and $x_{ci}$, $y_{ci}$ are the x- and y-coordinates of a point in the ith region of h, $h_i$, usually the center of that region. Even though each region may be expressed by the same function $C_C$, each region may have its own CCi value due to the shift in x- and y-coordinates, such that among two different regions, the respective CCi values may be different. CCi value is also affected by through hole opening sizes and/or shapes. In other words, if through hole opening sizes and/or shapes in two regions are different, functions and values of CCi in these two regions may also be different. In some embodiments, the forward projections through at least two regions overlaps. Note that formula (7) is an example and is not limiting different ways to divide regions and calculate forward projection for each individual region. In some embodiment, the small regions $h_i(z)$ all contains a subset of openings of h, and at least one of the small regions does not contain all openings of h. For example, in equation (7), $\hat{f}^{(K)}(z)$ may be used as a whole, or being partitioned into small regions and summed together as in equation (6). In another example, frequency domain equivalence of equation (7) may be used for calculation. In yet another example, one or more individual regions may be omitted from equation (7), such as for trading-off calculation speed as long as the accuracy level of calculation can still be satisfied.

FIGS. 3A and 3B illustrate a top view and corresponding matrix h of an exemplary collimator 104. The specific collimator illustrated in FIG. 3A is a MURA 11 NTHT (no-two-holes-touching) pattern. A NTHT pattern is an extension of a basic pattern where a row of all zeros is inserted between every two adjacent rows and a column of all-zeros is inserted between every two adjacent columns of the basic pattern. As a result, the minimal hole-to-hole distance is at least two times of the hole size. The black dots in FIG. 3A represent the holes on the collimator 104, which corresponds to the "one"s in the matrix h in FIG. 3B. For the matrix in FIG. 3B, there is an all-zeros column to the right with respect to the holes in FIG. 3A which is part of the MURA 11 pattern. Dash lines present a way of partitioning collimator 104 into 4 regions that can be used in equation (7). In this specific example, collimator 104 is divided into 2×2 regions. Also note that in this illustrated embodiment, each hole belongs to one and only one region after the partition, and none of the regions has all of the holes. The partition is not limited to 2×2 regions. Alternatively, collimator 104 can be divided into regions of any suitable number, such as a×b regions, where a and b represent any suitable integer, and all openings are divided into these regions and no openings appears in more than one region in some embodiments. Further, in some embodiments, a may be equal to b (a=b). In some alternative embodiments, a may not be equal to b (a≠b). In FIG. 3A, '+' marks are overlay on collimator 104 to represent the position $(x_{ci}, y_{ci})$ used to calculate CCi for each region. In the illustrated embodiment, position $(x_{ci}, y_{ci})$ is selected at the center of each region.

Figure 4B:
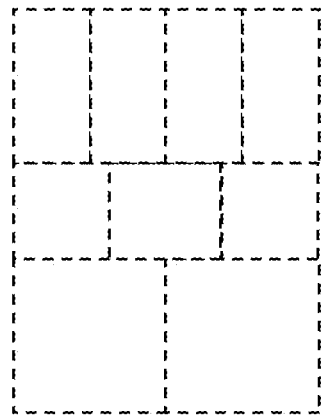
FIGS. 4A, 4B, and 4C are exemplary embodiments in partitioning regions on a collimator according to various aspects of the present disclosure.
Figure 4C:
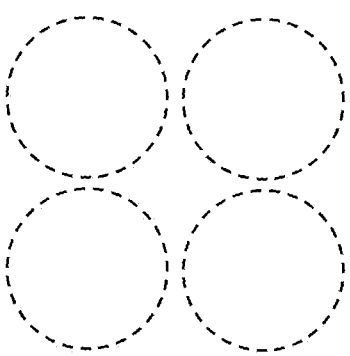
Figure 4A:
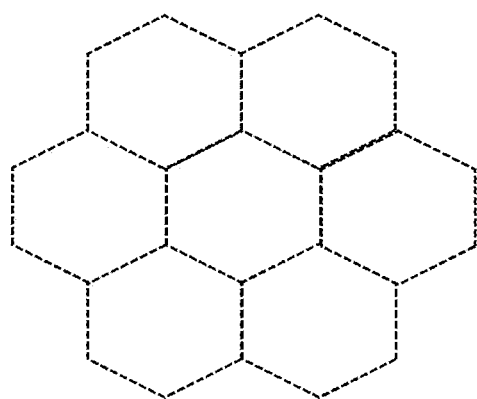

FIGS. 4A-4C illustrate various embodiments in partitioning regions on a collimator. Holes on collimator are omitted in FIGS. 4A-4C for simplicity. Each region may independently have its own shape and size. In some embodiments, each region does not overlap with any neighboring region. In some embodiments, two or more regions may have overlapping, such as to simplify a partition process, as long as the accuracy level of calculation can still be satisfied. In FIG. 4A, each region has a hexagon shape and the same size. In FIG. 4B, the regions are a combination of squares and rectangles with different sizes. Further, regions may be abutted with or separated from neighboring regions. FIG. 4C shows circular regions spaced from each other. In some embodiments, each region has a convex shape (no inner corner larger than 180 degrees). In some embodiments, each region has at least one hole. If a region has no holes or has only holes that no substantial radiation from the field of view would pass through, then it has little or no contribution to the calculation and hence can be ignored. But it is not necessary for each region to have same number of holes. Some regions may have more holes than others, or vice versa. Further, holes in the same region may have the same shape, but different between regions. For example, holes in square regions in FIG. 4B may be circular, while holes in rectangular regions in FIG. 4B may be square. In one embodiment, the holes in one or more of regions form coded aperture patterns, such as MURA patterns. The regions may be of different sizes, and the coded aperture patterns in the regions may be in different size, shape, or orientations. Furthermore, holes in the same region may have the same size, but different between regions. In one embodiment, the hole sizes in the central regions may be larger (wider acceptance angle), and become smaller toward the peripheral regions. For regions having different hole sizes, corresponding angular effect correction factors CCi also have different function and thereby different values as explained above. In other words, CCi may not be a constant but depending on regions. In furtherance of some embodiments, even within the same region, there may be holes of different sizes and/or shapes. A calculation of CCi of such a region may include first calculating different functions corresponding to different hole sizes and/or shapes, and then calculating an average of these different functions as a value for CCi. As an example, the calculation of the average may include weighing each function based on its corresponding holes' amount percentage in the total number of holes then summing the weighted functions.

It is worth to note that the computation of $p_r$ in equation (7) may include other elements such as penetration and background noise. However, the contribution of the above formula is a major component of $p_r$ which account for more than half of the signal strength. Since convolution and correlation are mirror operations, the following equation computing backward projection (or back projection) from respective forward projection can be used in the computations $$q(z) = \sum_{i=1}^{n} [r(z) \otimes h_i(z)] \times C_{Ci} \quad (7\text{-}1)$$

where $r(z) \otimes h_i(z)$ is the backward projection of the ith region of the collimator, $C_{Ci}$ is the angular correction for the ith region. By computing backward projection of each region, q(z) as overall backward projection can be computed as a sum of the backward projections of each region. And r(z) can be the quotient inside the bracket in equations (7-1) or (7-2).

$$r(z) = \frac{p - \sum_{z \neq z'} p_r(z')}{p_r(z)} \quad (7\text{-}2)$$

or $$r(z) = \frac{p}{\sum_z p_r(z)}. \quad (7\text{-}3)$$

Either equation (7-2) or (7-3) can be considered as comparing the measured image p with forward projections. The partition of h used in equation (7-1) for computing backward projection may or may not be the same as the partition of h used in equation (7) for computing forward projection. For example, to compute backward projection, h may be partitioned into more regions than when it is partitioned to compute respective forward projection. Alternatively, to compute backward projection, h may be partitioned into regions of different shapes than when it is partitioned to compute respective forward projection. In an example, frequency domain equivalence of equation (7-1) may be used for calculation. In another example, one or more individual regions hi may be omitted from equation (7-1), such as for trading-off calculation speed as long as the accuracy level of calculation can still be satisfied.

Note that the method is an iterative method where $\hat{f}^{(k+1)}$ is the (k+1)th estimate of the object image. The iteration in eq. (5) can be simplified as $$\hat{f}^{(k+1)}(z) = \hat{f}^{(k)}(z) \times q(z) \tag{7-4}$$

The value of q(z) may first be normalized before calculating $\hat{f}^{(k+1)}$.

It is worth to note that forward projections can be used in other applications such as simulation, i.e., generating simulated projections for a given or virtual object, their calculations can be done through (7) as well. The partition of h does not have to be same for all iterations. The number of regions to divide h into is a consideration trading off reconstructed image quality and computation speed. The regions in a partition can be very small, and may even contain only one hole. Smaller regions with fewer holes represent better approximation to the small angle approximation and higher precision, but may slow down computation speed, while larger regions with more holes may increase computation speed but with poorer image quality. The smaller the region $h_i$ is, it is usually more accurate, but the computational complexity is higher as well. Therefore, the partition can start coarsely (smaller number of regions) in the beginning for faster computation, and finer partitions (larger number of regions) can be used as iterations progress.

In SPECT imaging, multiple planar images are acquired from different angles by rotating camera around the object (e.g., patient 150). When coded aperture mask is used for collimation, a 2D or 3D image can be reconstructed from one planar image, such as applying equations (6) and (7). Note that in equations (6) and (7), p or $p_c$ are used, which represents one planar image, meaning f is estimated using one acquired planar image. The iterations in eq. (4), (5)-(5-2), can all be simplified as $$\hat{f}_j^{(k+1)}(z) = \hat{f}_j^{(k)}(z) \times q_j(z) \tag{8}$$

where $q_j$ is the updating factor for jth element of f(z).

This invention also presents methods to reconstruct object image using more than one acquired planar images, which may be acquired from different angle, or with different distance from the object, or different distance of collimator to detector, or with shift, tilting of camera (detector) or object, or a combination of two or more of the above. Because more data are used to reconstruct the image, the accuracy and signal-to-noise ratio may be higher. When more than one acquired planar images are used, the updating factor can be $$q_j(z) = \sqrt[m]{\sum_{t=1}^{T} q_j^m(z, t) / T} \tag{9}$$

or $$q_j(z) = \sqrt[T]{\prod_{t=1}^{T} q_j(z, t)} \tag{10}$$

where T is the number of projections used, and m is a positive number, and $q_j(z, t)$ is the updating factor for element j of f(z) calculated by the method presented in this invention using the tth acquired image alone. Note that when the underlying grid of the coordinate system $q_j(z, t)$ is different from each other (i.e., for different t), interpolation and/or rotation/flip may be performed so that all of them are defined on the same grid.

A special case of an embodiment of this method is to update f using two opposite projections. In such scenario, since the slices in the 3D images are in X-Y plane and parallel to the detector surface in both acquisition positions, only axis flip is needed but no rotation computation is required in calculating equation (9) or (10). Since many clinical SPECT systems employ two cameras mounted at opposite positions where two opposite projections are acquired simultaneously, this embodiment has the advantage of processing the pairs of two opposite projections as they are acquired, streamlining the data flow. Another special case of the embodiment of this method is to update f using two opposite projections (images acquired with 180 degrees apart), and two projections perpendicular to the previous two opposite projections. Since the slices in the 3D images are parallel to the detector surface, the axes of these orthogonal projections are aligned with some axis permutation, no rotation may be needed in calculating equation (9) or (10).

Figure 5:
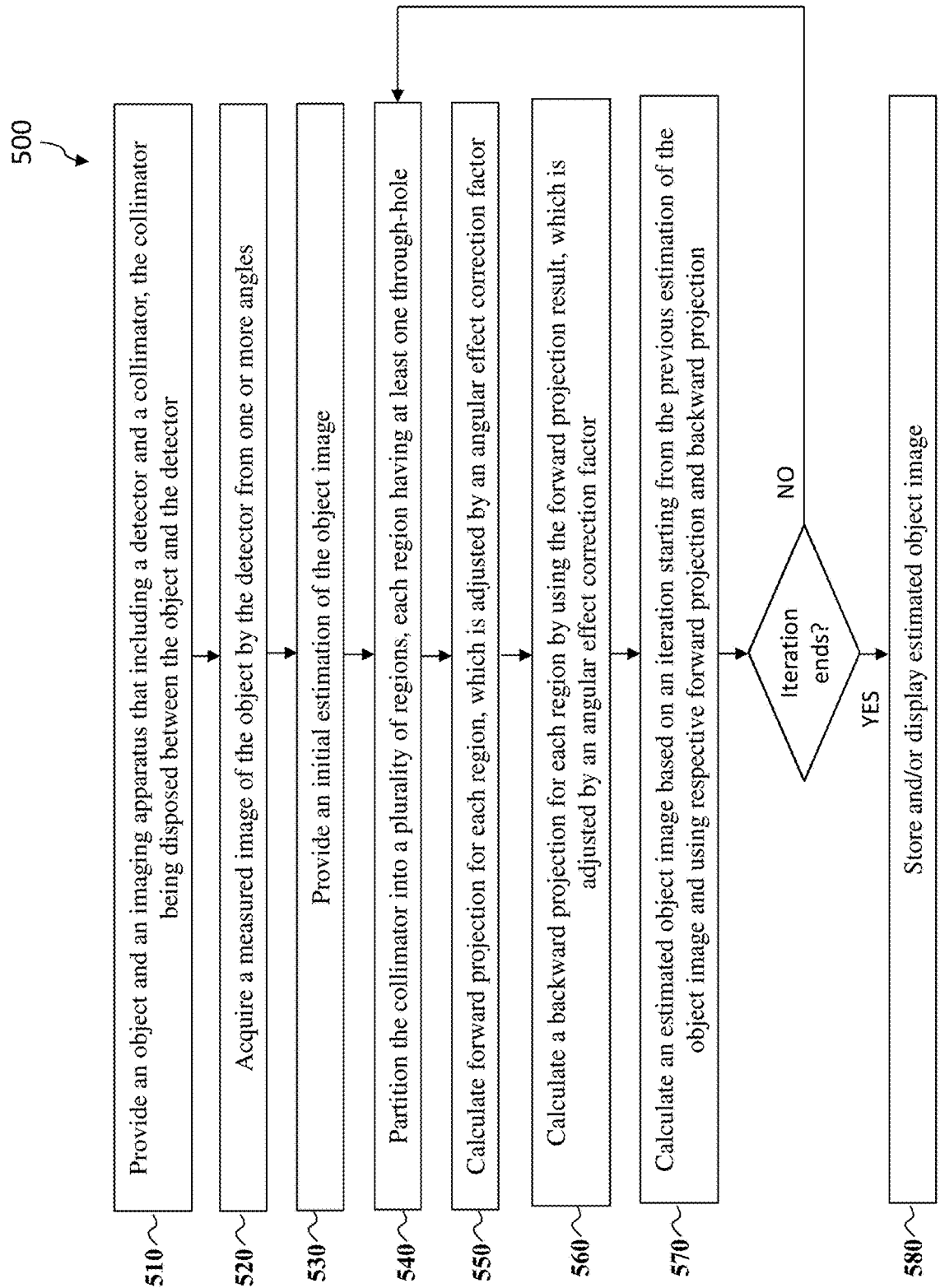
FIG. 5 is a flow chart of a method of image reconstruction according to various aspects of the present disclosure.

Referring now to FIG. 5, a flow chart of a method 500 for image reconstruction for collimator and detector based medical imaging systems is illustrated according to various aspects of the present disclosure. The method 500 is merely an example and is not intended to limit the present disclosure to what is explicitly illustrated in the method 500. Additional operations can be provided before, during, and after the method 500, and some operations described can be replaced, eliminated, or moved around for additional embodiments of the method. The method 500 is described below in conjunction with FIGS. 1-4.

At operation 510, an object (e.g., patient 150) and an imaging apparatus (e.g., imaging apparatus 100) is provided. The imaging apparatus includes a collimator (e.g., collimator 104) and a detector (e.g., detector 102). The collimator is disposed between the object and the detector. At operation 520, the collimator filter photons emitted from the object and the detector acquire a measured image from the photons arriving at the detector. The imaging apparatus may rotate around the object to acquire multiple measured images from multiple angles. In one example, the imaging apparatus acquires measured images from 0°, 90°, 180°, and 270° angles surrounding patient 150.

At operation 530, an initial estimation of the object image ($\hat{f}^{(0)}$) is provided as the starting point of the iteration process. A proper initial guess may be used for $\hat{f}^{(0)}$, such as a matrix of all "one"s. In another example, a Computed Tomography (CT) image may be used for $\hat{f}^{(0)}$. Modern molecular imaging systems are often delivered in hybrid form with CT scanners in tandem, such as a hybrid SPECT/CT or PET/CT systems. CT images are created with X-ray passing through an object, such as a patient lying on a couch undergoing SPECT or PET imaging. When a CT scan is available prior to SPECT reconstruction, the CT scan can be used to generate the initial guess. In one embodiment, the CT scan can be used as a finite support, i.e, the contour of the patient body can be used to define the scope of "one"s in the matrix mentioned above, setting the matrix element values to be "one" inside the patient contour and "zero" if outside.

The method 500 then moves to operation 540 to start an iteration process. The iteration process (also includes operations 550-580) may be executed by the computer system 130, such as by the image processor 134. At operation 540, the collimator is partitioned into a plurality of regions. Each region has at least one hole. A matrix corresponding to the collimator is also partitioned accordingly.

At operation 550, the method 500 calculates a forward projection from an estimation of the object image and a partitioned matrix representing each region, such as from a convolution using equation (7) or an MLEM method using equation (7-4) in various embodiments. The forward projection is also adjusted by an angular effect correction factor(s) of each region including a $\cos^3(\theta)$ term and aperture collimation effect term.

At operation 560, the method 500 calculate a backward projection from the forward projection result from previous operation, such as by using a correlation operation described in equation (7-1). The backward projection is also adjusted by an angular effect correction factor of each region including a $\cos^3(\theta)$ term. Calculating backward projection may use the same partition as the one used in respective forward projection, or alternatively may use a different partition, such as with different numbers and/or shapes of regions. Operation 560 may further include intermediate steps, such as calculating r(z) using p and $p_r(z)$ in equations (7-2) and (7-3). Further, r(z) may be interpolated to different grid size. Subsequently r(z) is used to calculate backward projection.

At operation 570, the method 500 reconstructs the object image using the calculated backward projection from previous operation, such as using equation (8). Method 500 then determines whether iteration may end, such as by predetermined iteration steps or when difference of f between consecutive iterations are below a predetermined threshold (e.g., <0.5%). If the iteration does not end, then the $\hat{f}^{(k)}$ will be used for next iteration as an input for operation 540 to calculate $\hat{f}^{(k+1)}$. Operation 540 may repartition the mask to get finer meshing (e.g., more number of regions) for higher accuracy. If the iteration ends, method 500 proceeds to operation 580 that the estimated object image is stored (e.g., in image storage 136) and/or displayed (e.g., on display 138).

Figure 6:
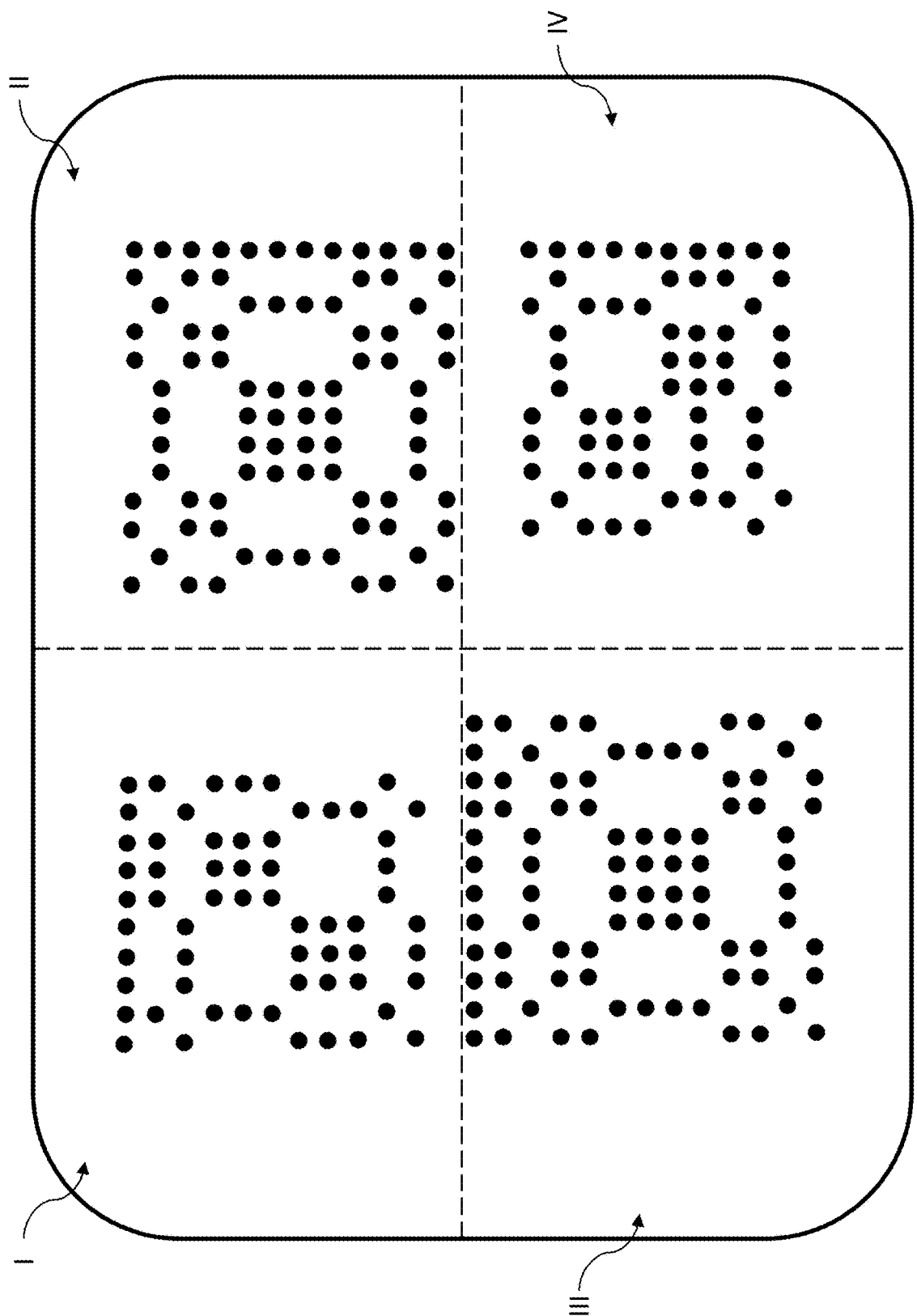
FIG. 6 is an exemplary collimator design having a plurality of regions therein, where each region includes a coded aperture pattern, according to various aspects of the present disclosure.
Figure 7:
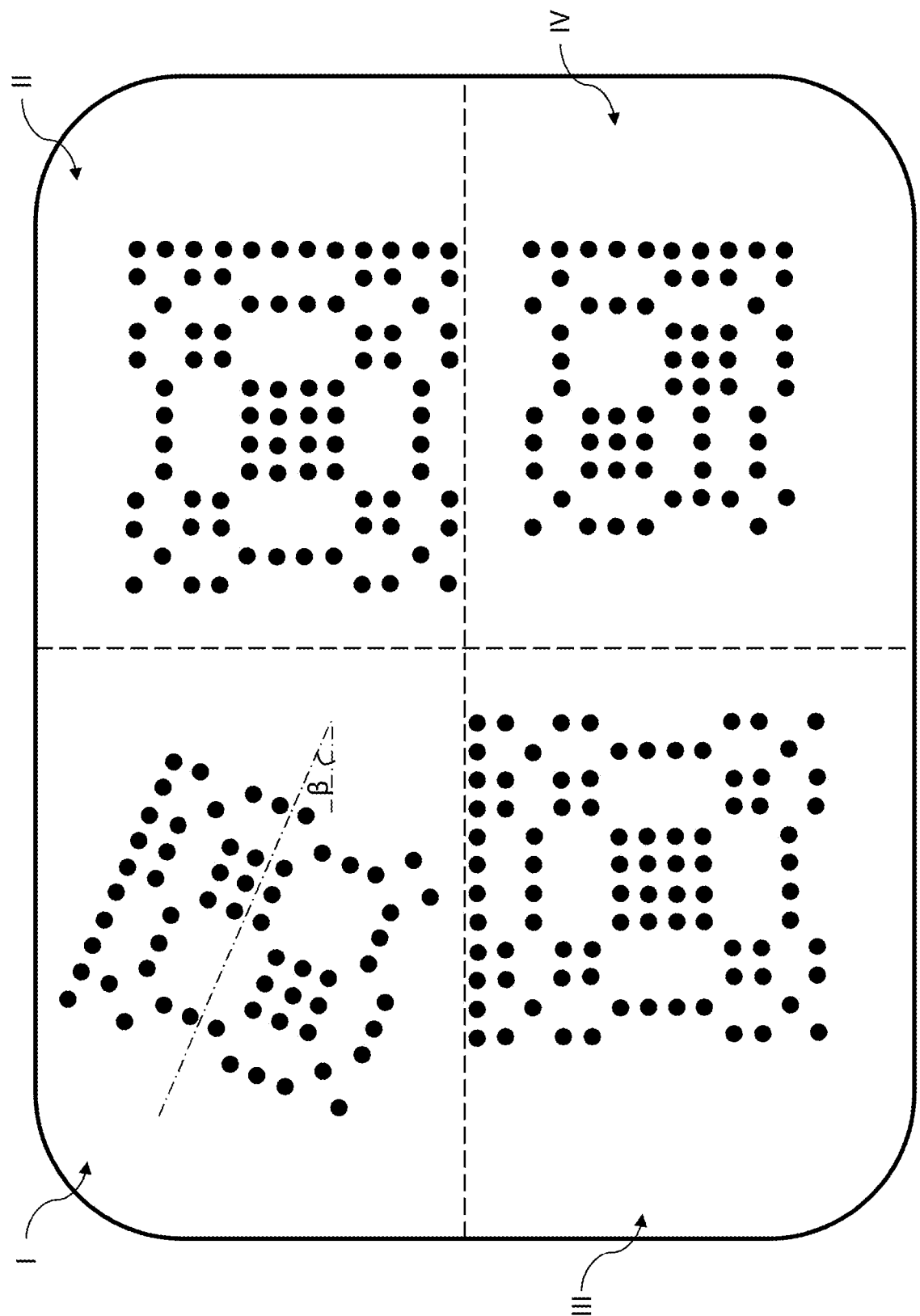
FIG. 7 is an exemplary collimator design having a plurality of regions therein, where one region has a rotated pattern with respect to patterns in other regions.

Dividing a collimator into multiple regions and calculating forward and backward projections associated with respective individual regions provide a possibility of a novel collimator design. In one example, when the collimator is represented in matrix form, h, less than 70% of the elements are ones. More specifically, for example, for common coded aperture collimators such as those in URA and MURA arrays, the number of ones is less than 50% of total number of elements. An exemplary collimator design is illustrated in FIG. 6. As discussed above, collimator can be considered as a metal plate with a plurality of holes, such as through holes. In FIG. 6, a black dot represents a hole. In traditional coded aperture design, the holes on the whole collimator form one specific coded pattern, such as a URA array or a MURA array. As a comparison, the collimator in FIG. 6 is divided into a plurality of regions (or groups) (e.g., regions I, II, III, and IV), and through holes in each region by themselves independently form a coded aperture pattern, including but not limited to: URA array, MURA array, random array, and pseudo random array. In a specific embodiment, each region has a unique pattern selected from either a URA array or a MURA array. The pattern may not be the same for all groups, the hole sizes and shapes may also be different, or the orientation of rows or columns of holes in the individual groups may be different. An exemplary collimator with a region of different orientation is illustrated in FIG. 7. In FIG. 7, compared with patterns in regions II, III, and IV, the pattern in region I has an orientation with respect to a normal direction to the top surface of the collimator. This orientation is denoted as an angle β. In various embodiments, the angle β may be in a range from about 5 degrees to about 85 degrees, such as 45 degrees. The holes can be regarded as landing on a meshing grid on the collimator. In some embodiments, a grid in one region may be different than those in other regions. For example, one region may have larger grid size than others, or smaller vice versa. The illustrated collimator in FIG. 7 can also be regarded as having a different grid in region I than others. Although the collimators illustrated in FIGS. 6 and 7 have four groups of coded aperture patterns, in various embodiments, a collimator may have other number of groups, such as two, three or more than four groups. In a particular example, a collimator may have 9 groups of coded aperture patterns in a 3×3 array.

The holes in different groups on the same plate can be of different sizes and different shapes. Furthermore, the holes in the same group can be of different sizes and different shapes. Since the incident angle θ (FIG. 2B) is generally defined by the hole size and length, different holes in the same collimator may have different incident angles. In some embodiments, the minimum incident angle θ of all the holes in the collimator is at least 10°, such as at least 15° in some specific examples, which has the benefit of a larger FOV. The FOV of each group may overlap with at least one other group on the same plate (within the designed range of imaging: usually the FOV is bigger when it is farther away from the collimator or aperture). In some embodiment, the distance between the groups (the minimum hole-to-hole distance between two different groups) is larger than the minimal hole-to-hole distance within each group, may be more than twice the minimal hole-to-hole distance within each group, for example at least 2.5 times the minimal hole-to-hole distance within each group. In one embodiment, the minimal hole-to-hole distance within each group is less than 2 times the hole size. Hole size is defined as a size of smallest square that can fully covers the hole. Hole-to-hole distance is a pitch defined by the distance from the center of one hole to the center of an adjacent hole. In some embodiments, the number of holes can be larger than 30. For example, in each region, there can be one of 12, 24, 60, 84, 144, 180, and 264 holes in a MURA 5, 7, 11, 13, 17, 19 and 23 patterns. In some other embodiments, a collimator mask may have a mosaic of 4 identical MURA coded aperture patterns organized in a 2-by-2 form with the separation between the neighboring holes from different groups being the same as the spacing between holes of the same group. The four patterns are identical in size, shape, and orientation. The reconstruction method presented in this invention is also applicable to this type of collimators by partitioning the holes in the groups, including a 2-by-2 partition. Further, in some embodiments, the density of the holes in the collimator is less than 50%, typically less than 35% or 30%. And in some embodiments, the density of the holes in the collimator is greater than 2%, typically greater than 5% or 7.5%. The density of the holes in the collimator is defined as the total area of the holes (total opening) over the area of the smallest convex polygon that can surround all the holes. In case of hole shapes other than straight through holes, such as knife-edge or channel-edge holes, the smallest section of the hole area is used in the calculation of total hole area. Similarly, in some embodiments, the density of the holes in each region is less than 50%, typically less than 35% or 30%. And in some embodiments, the density of the holes in each region is greater than 2%, typically greater than 5% or 7.5%. The density of the holes in a region is defined as the total area of the holes (total opening) in that region over the area of the smallest convex polygon that can surround all the holes in that region. Similarly, in case of hole shapes other than straight through holes, such as knife-edge or channel-edge holes, the smallest section of the hole area is used in the calculation of total hole area.

This invention also presents methods that integrate a multi-resolution (or multi-scale) scheme, which allows the computational complexity to be reduced significantly. Multi-resolution is an effective strategy relating to image processing, analysis, and reconstruction. In short, the process may start at a lower resolution, and evolve to higher resolution as the process progresses.

Figure 8:
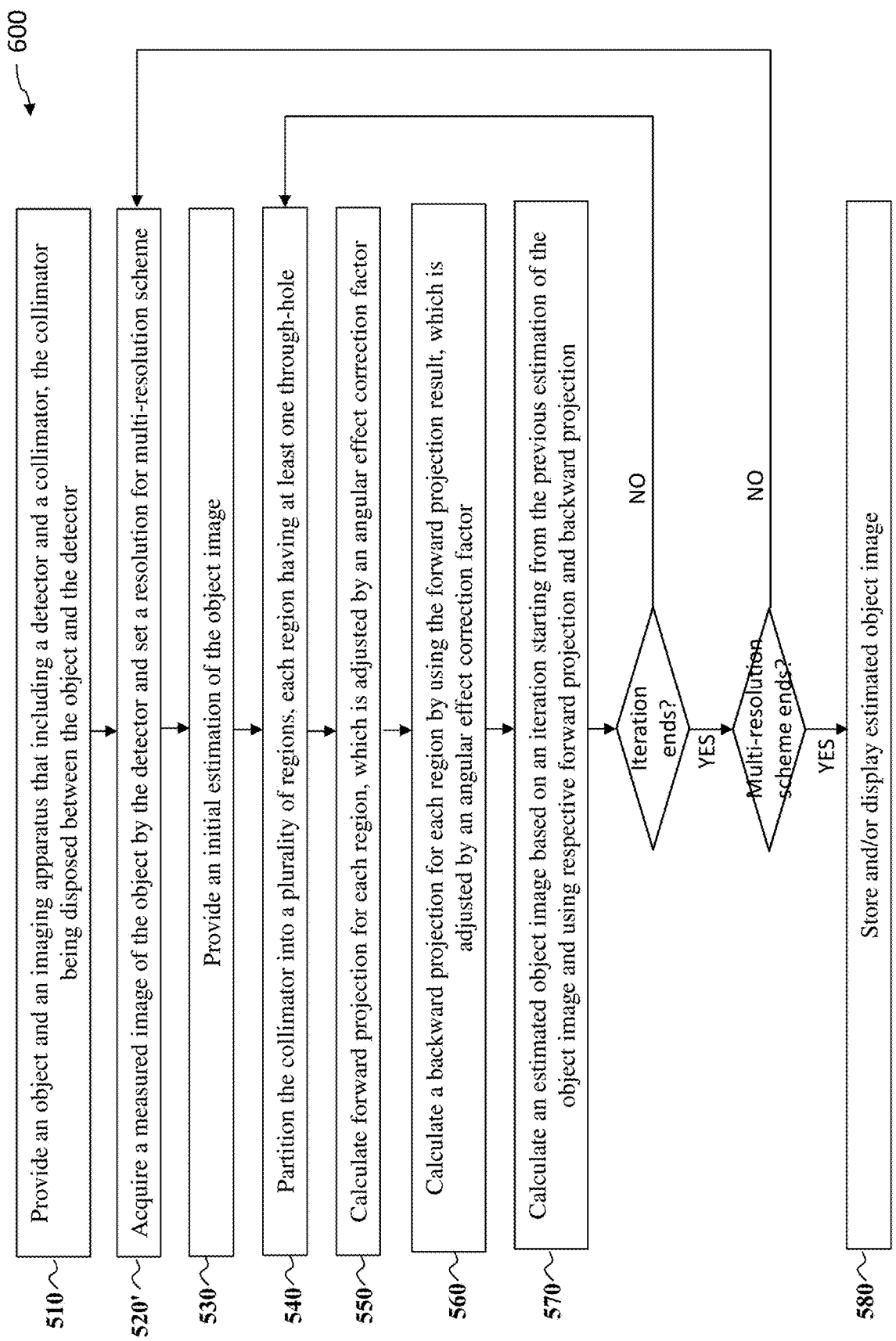
FIGS. 8, 9, and 10 are flow chats of methods of image reconstruction with multi-resolution schemes.

Referring now to FIG. 8, a flow chart of a method 600 for image reconstruction for medical imaging systems based on multi-resolution scheme of measured image of the object is illustrated according to various aspects of the present disclosure. The method 600 is merely an example and is not intended to limit the present disclosure to what is explicitly illustrated in the method 600. Additional operations can be provided before, during, and after the method 600, and some operations described can be replaced, eliminated, or moved around for additional embodiments of the method. At operation 510, an imaging apparatus including at least a collimator and at least a detector is provided. The collimator is disposed between the object and the detector. At operation 520', the collimator filters photons emitted from the object (e.g., near-field radiation) and the detector acquires a measured image from the photons arriving at the detector. Different from operation 520 in the method 500, operation 520' may generate a series of measurements with varying resolutions from the original measurements. Usually this can be done by applying a low-pass filter to the original measurements, then down-sample them to reduce data sizes (dimensions). Then the multi-resolution method 600 proceeds to operations 530-570 in reconstructing images of the objects from measurements of the lowest resolution or scale; then use the reconstructed image as initial guess to reconstruct another image of the object from another measurement of a higher resolution. Operation 530 may also include adjusting a resolution of the estimation of the object image to a different level that matches the selected measurement resolution. For example, operation 530 may include resolution conversion of an estimated object image from previous resolution level to next resolution level by up-sampling or down-sampling. Operations 540, 550, 560, and 570 are substantially similar to what have been discussed above with reference to the method 500 in FIG. 5 and the respective descriptions will be skipped for the sake of simplicity. The method 600 may repeat the process until the measurements of the original resolution are used to reconstruct the image of the object. In some embodiments, the method 600 may repeat the process until using a resolution lower than or higher than the measurements of the original resolution to reconstruct the image of the object. Because the images and measurements at lower resolutions usually have lower dimensions (smaller matrix sizes), the computational complexity is reduced significantly this way, therefore enables faster convergence and helps avoid local minima in some cases.

Figure 9:
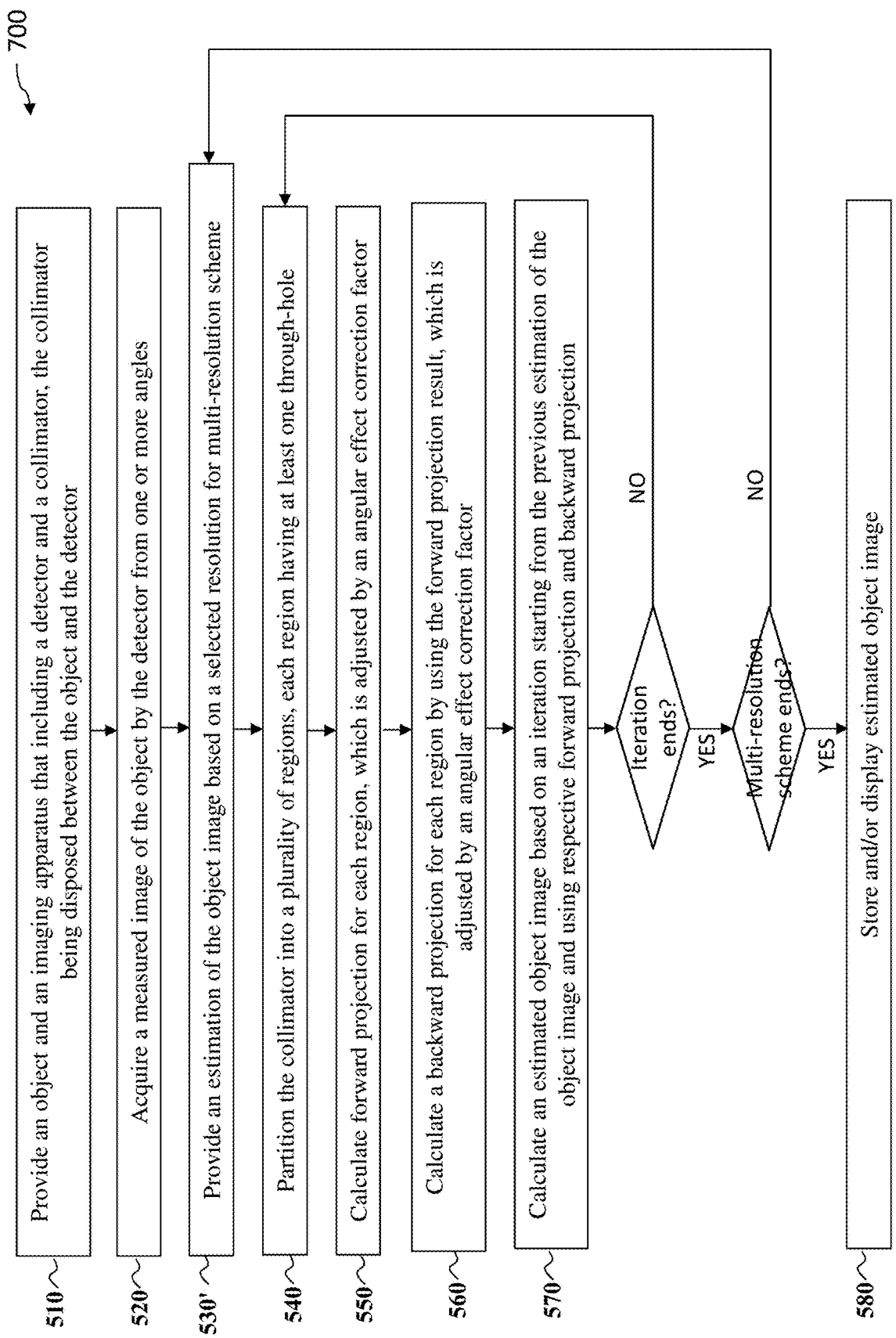

Besides using the original measurements to generate a series of measured image with different resolutions, estimation of the object image can also be used to generate a series of projections with different resolutions for image reconstruction using a multi-resolution scheme. Referring now to FIG. 9, a flow chart of a method 700 for image reconstruction for medical imaging systems based on a multi-resolution scheme of estimation of the object is illustrated according to various aspects of the present disclosure. The method 700 is merely an example and is not intended to limit the present disclosure to what is explicitly illustrated in the method 700. Additional operations can be provided before, during, and after the method 700, and some operations described can be replaced, eliminated, or moved around for additional embodiments of the method. At operation 510, an imaging apparatus including at least a collimator and at least a detector is provided. The collimator is disposed between the object and the detector. At operation 520, the collimator filters photons emitted from the object and the detector acquires a measured image from the photons arriving at the detector. At operation 530', an estimation of the object image is provided as the starting point of the iteration process. Different from operation 530 in the method 500, operation 530' may start with an estimation of a low resolution and replace it by another estimation of a higher resolution. For example, this can be done by optionally applying a low-pass filter to the original estimation, then down-sampling them to reduce data sizes (dimensions). Then the multi-resolution method 700 proceeds to operations 540-570 to reconstruct images of the objects based on the estimation of the lowest resolution or scale; then use the reconstructed image as an initial guess to reconstruct another image of the object. Operations 540, 550, 560, and 570 are substantially similar to what have been discussed above with reference to the method 500 in FIG. 5 and the respective descriptions will be skipped for the sake of simplicity. The iteration generates an estimated object image from previous resolution level, which will be converted to next resolution level, for example, by up-sampling, to use as the new estimation of the object image for operation 530'. The method 700 repeats the process until the highest resolution of the estimation is used to reconstruct the image of the object. In a particular embodiment, operation 530' starts with an initial guess of the object image at 6 mm resolution, then uses the reconstructed image at 2 mm resolution as the initial guess for a new round of calculation, until the resolution is down to 1 mm. Because the estimation at lower resolutions usually has lower dimensions (smaller matrix sizes), the computational complexity is reduced significantly this way, therefore enables faster convergence and helps avoid local minima.

Figure 10:
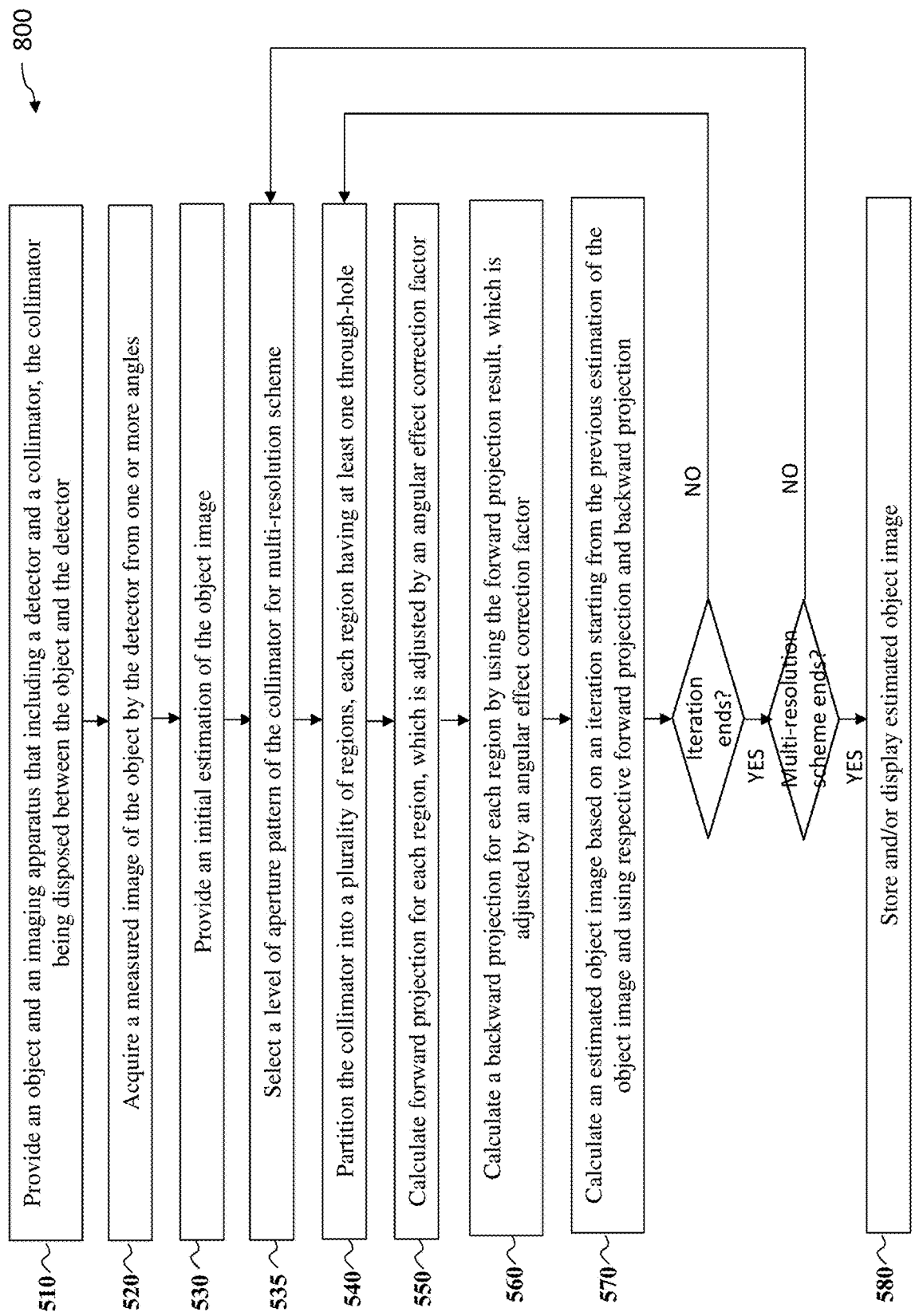

Furthermore, depending on the design, a collimator may provide multiple levels of aperture patterns, such as a first level of aperture pattern at a lower resolution and a second level of aperture pattern at a higher resolution. An illustration of embodiments of such collimators will be further discussed below in association with FIGS. 11 and 12. Referring now to FIG. 10, a flow chart of a method 800 for image reconstruction for collimator and detector based medical imaging systems based on multi-resolution scheme of aperture patterns provided by the collimator is illustrated according to various aspects of the present disclosure. The method 800 is merely an example and is not intended to limit the present disclosure to what is explicitly illustrated in the method 800. Additional operations can be provided before, during, and after the method 800, and some operations described can be replaced, eliminated, or moved around for additional embodiments of the method. At operation 510, an imaging apparatus including at least a collimator and at least a detector is provided. The collimator is disposed between the object and the detector. At operation 520, the collimator filters photons emitted from the object and the detector acquires a measured image from the photons arriving at the detector. At operation 530, an estimation of the object image is provided as the starting point of the iteration process. At operation 535, the method 800 selects a first level of aperture pattern as a collimator at a lower resolution. Then the multi-resolution method 800 proceeds to operations 540-570 to reconstruct images of the object from the collimator at the lower resolution; then use the reconstructed image as initial guess to reconstruct other images of the object from a second level of aperture pattern as a collimator at a higher resolution. Operations 540, 550, 560, and 570 are substantially similar to what have been discussed above with reference to the method 500 in FIG. 5, including partitioning the collimator at different resolution levels, and the respective descriptions will be skipped for the sake of simplicity. In some embodiments, the forward projection operation 550 and backward projection operation 560 involve the use of aggregated or average angular effect correction for the group of holes. The method 800 repeats the process by operating at different levels of resolution, i.e., using measured projection image, estimated object image and collimator pattern at corresponding resolution levels, until the aperture pattern of the collimator at the highest resolution are used to reconstruct the image of the object. Because the collimator at lower resolution provides smaller matrix sizes, the computational complexity is reduced significantly this way, therefore enables faster convergence and helps avoid local minima.

In some embodiments, an image reconstruction method may include using two or three multi-resolution schemes, including measurements and estimations of the object at various resolutions or scales, and different levels of aperture patterns of a collimator at different resolutions, which provides flexibility for enabling fast convergence.

An exemplary collimator design with multiple levels of aperture patterns is illustrated in FIG. 11A. As discussed above, collimator can be considered as a metal plate with a plural of holes. In FIG. 11A, a white block represents a hole. In the illustrated embodiment, the collimator has a 15×15 aperture pattern. The collimator has holes arranged in groups (e.g., 5×5 groups as marked by white dotted lines). The groups may or may not have holes, represented with 1 or 0, respectively. As shown in FIG. 11B, each group represented as 1 may have four holes arranged in a 3×3 array, but it may also have a different number of holes, and the numbers of holes in the groups may be different. In the illustrated embodiment, through holes in each group form a coded aperture pattern, including but not limited to: URA array, MURA array, random array, and pseudo random array. In a specific embodiment, each region has a unique pattern selected from either a URA array or a MURA array. In FIG. 11B, the 3×3 array forms a MURA 3×3 array. Further, in some embodiments, the groups may have more than one pattern. For example, there may be at least one group having a pattern different from that of the other groups, such as an array of different number of holes, different numbers of columns or rows, and/or different coded aperture patterns. As also shown in FIGS. 11A-B, the holes may be square, or they may be round, but they may also be formed in other shapes such as hexagonal, triangular, ovoid, rectangular, etc. The holes illustrated are all the same shape (i.e., either square or circular) and all the same size; however, it is possible that a collimator according to an embodiment of the present invention may have some groups with one shape of hole (e.g., square) and other groups with a different shape of hole (e.g., round). Furthermore, cross sections of the holes may be different among groups. For example, the holes of different cross sections may include straight through holes, knife-edge holes, and/or channel-edge holes. Additionally, the sizes of the holes may be different for one group than another (thus offering the possibility that groups having smaller holes may optionally have more holes within that group). Moreover, the holes within one or more groups may differ from each other in size, shape and/or spatial orientation. It may be easier to make and use a collimator fashioned according to an embodiment of the present invention wherein the holes are uniform within a group, and also uniform from group to group, in terms of shape, size and centeredness. However, there may be some applications where having different hole shapes, sizes and/or centeredness/orientations may be beneficial, such as when the collimator is designed for special applications where it may be desired to accept photons from a particular organ or region of interest differently from surrounding or nearby tissue. Also, there may be some detector arrangements (e.g., non-uniform distributions, shapes or sizes of pixels), some imaging procedures, and/or some reconstruction/calibration schemes or algorithms (e.g., utilizing differential photon acceptances) that are particularly well suited to using non-uniform hole shapes, sizes and/or centeredness/orientations within groups and/or from group to group as described above.

By regarding each hole as an individual pixel, the collimator provides a 15×15 aperture pattern, as corresponding to a higher-resolution aperture pattern, as shown in FIG. 11A. Alternatively, by regarding each group as an individual pixel, as shown in FIG. 11C, the plurality of groups provides a 5×5 coded aperture pattern, as corresponding to a lower-resolution aperture pattern, where each group is represented by either 1 or 0. The coded aperture pattern may be one of URA array, MURA array, random array, and pseudo random array. In the illustrated embodiment, the 5×5 coded aperture pattern is a MURA 5×5 array. Thus, a single collimator, such as the one illustrated in FIG. 11A, provides two levels of resolutions. Accordingly, in a multi-resolution image reconstruction operation, such as the method 800 discussed above in association with FIG. 10, the multi-resolution scheme may start with the coarser aperture pattern at a lower resolution (e.g., MURA 5×5 array in FIG. 11C) and subsequently evolve to the lower-level aperture pattern at a higher resolution (e.g., 15×15 aperture pattern in FIG. 11A with MURA 3×3 array in each group). By having coded aperture patterns in both levels, it improves spatial resolution, sensitivity and signal-to-noise ratio (SNR) of constructed images.

In the illustrated embodiment in FIGS. 11A-C, the coded aperture pattern at the higher level (e.g., a MURA 5×5 array) formed by groups is different from the coded aperture pattern in each group (e.g., a MURA 3×3 array). In some embodiments, both coded aperture patterns may be the same. For example, a collimator with a 25×25 aperture pattern may have 5×5 groups with holes of a MURA 5×5 array in each group, while the 5×5 groups form a MURA 5×5 array at the higher level. Both MURA 5×5 arrays may be the same. Alternatively, both MURA 5×5 arrays at the two levels may be different. In some other embodiments, the coded aperture pattern at the higher level may be larger or smaller than the coded aperture pattern in each group. For example, a collimator with a 35×35 aperture pattern may have 5×5 groups with holes of a MURA 7×7 array in each group, while the 5×5 groups form a MURA 5×5 array (i.e., smaller than a MURA 7×7 array) at the higher level. The particular sizes of the MURA array illustrated herein are not intended to be limiting. For example, the coded aperture pattern formed by groups may be one of a MURA 5×5 array, a MURA 7×7 array, a MURA 11×11 array, and other suitable arrays; the coded aperture pattern formed in each group may be one of a MURA 5×5 array, a MURA 7×7 array, a MURA 11×11 array, and other suitable arrays.

In the illustrated embodiment in FIGS. 11A-B, each group has the identical coded aperture pattern (e.g., the same MURA 3×3 array in FIG. 11B). Herein, two coded aperture patterns are referred to as identical when in a top view holes in the respective two groups can overlap with each other in a hypothetical shifting (without rotation). If the position arrangement of the holes in one group is different from that in the other group, or there are hole dimensions (e.g., hole shapes, sizes/lengths, spacing, and/or cross sections) are different between two groups, the two coded aperture patterns are referred to as not identical, or as different. Accordingly, one or more groups may have different aperture patterns, such as a transformation of an existing aperture patterns, from other groups. Referring to FIG. 12, the group located at the lower-right corner of the collimator in FIG. 12A has a different pattern from other groups, which is a transformation of the MURA 3×3 array in other groups. FIG. 12B illustrates several kinds of transformation, such as a transpose operation (e.g., rows become columns), a rotation operation (e.g., a counter-clock-wise 90° rotation), and a shifting operation (e.g., the first column becomes the last column with shifting of middle columns). The other transformation may also include a flip operation (e.g., front side becomes back side). The one or more groups with transformed coded aperture patterns may locate in any places of the collimator, such as edges and centers but not limited to corners. Such arrangement may be suitable for special applications where it may be desired to accept photons from a particular organ or region of interest differently from surrounding or nearby tissue.

Although not intended to be limiting, one or more embodiments of the present disclosure provide many benefits for molecular imaging of a subject such as a patient. For example, the image reconstruction methods increase imaging sensitivity and resolution even when a relatively large collimator not meeting small mask assumption is used. Therefore, system performance is improved.

The foregoing outlines features of several embodiments so that those of ordinary skill in the art may better understand the aspects of the present disclosure. Those of ordinary skill in the art should appreciate that they may readily use the present disclosure as a basis for designing or modifying other processes and structures for carrying out the same purposes and/or achieving the same advantages of the embodiments introduced herein. Those of ordinary skill in the art should also realize that such equivalent constructions do not depart from the spirit and scope of the present disclosure, and that they may make various changes, substitutions, and alterations herein without departing from the spirit and scope of the present disclosure. Accordingly, it is appropriate that the appended claims be construed broadly and in a manner consistent with the present disclosure.

What is claimed is:

1. A collimator for medical imaging, comprising:
a plate with a top surface and a bottom surface and holes extending from the top surface to the bottom surface, wherein:
the plate includes regions of a first type and regions of a second type that are arranged into an array;
each region of the first type includes at least one of the holes;
each region of the second type is free of any of the holes;
when the regions of the first type are given a first mathematical representation and the regions of the second type are given a second mathematical representation, the array forms a first coded aperture pattern; and
each region of the first type includes a second coded aperture pattern when each hole in the respective region is given the first mathematical representation and other areas in the respective region are given the second mathematical representation.

2. The collimator of claim 1, wherein the first coded aperture pattern is one of a URA array, a MURA array, a random array, and a pseudo random array.

3. The collimator of claim 2, wherein the first coded aperture pattern is a MURA array.

4. The collimator of claim 3, wherein the first coded aperture pattern is one of a MURA 5×5 array, a MURA 7×7 array, and a MURA 11×11 array.

5. The collimator of claim 1, wherein the second coded aperture pattern is one of a URA array, a MURA array, a random array, and a pseudo random array.

6. The collimator of claim 5, wherein the second coded aperture pattern is a MURA array.

7. The collimator of claim 6, wherein the second coded aperture pattern is one of a MURA 3×3 array, a MURA 7×7 array, and a MURA 11×11 array.

8. The collimator of claim 1, wherein the first coded aperture pattern is different from the second coded aperture pattern.

9. The collimator of claim 1, wherein the first coded aperture pattern is the same as the second coded aperture pattern.

10. The collimator of claim 1, wherein the at least one hole of at least two of the regions of the first type are different in either sizes or shapes.

11. The collimator of claim 1, wherein at least one of the second coded aperture patterns is a transformation of another of the second coded aperture patterns.

12. The collimator of claim 11, wherein the transformation includes one of a transpose operation, a rotation operation, a shifting operation, and a flip operation.

13. A collimating apparatus for medical imaging, comprising:
a plate with a top surface and a bottom surface; and
a plurality of holes, wherein each of the plurality of holes extends from the top surface to the bottom surface, wherein:
the plate includes two or more regions that are arranged into an array;
the array forms a first coded aperture pattern when the regions including at least one of the plurality of holes are given a first mathematical representation and the regions free of any of the plurality of holes are given a second mathematical representation; and
each of the two or more regions includes a second coded aperture pattern when each hole of the plurality of holes in the respective region is given the first mathematical representation and other areas in the respective region are given the second mathematical representation, wherein the second coded aperture patterns of at least two of the two or more regions are not identical.

14. The collimating apparatus of claim 13, wherein at least one of the first and second coded aperture patterns is one of a URA array, a MURA array, a random array, and a pseudo random array.

15. The collimating apparatus of claim 13, wherein the second coded aperture patterns in all the two or more regions are different from each other.

16. The collimating apparatus of claim 13, wherein the plate has a density of holes less than 50%.

17. An apparatus for medical imaging, comprising:
a collimator for filtering photons emitted from an object; and
a detector for acquiring an image from photons passing through the collimator,
wherein the collimator includes a plate with a top surface and a bottom surface and holes extending from the top surface to the bottom surface, the holes are distributed throughout the plate such that first regions of the plate are holey and second regions of the plate are opaque, the first and the second regions are arranged into an array and collectively form a first coded aperture pattern when each first region is given a first mathematical representation and each second region is given a second mathematical representation, wherein when each hole is given the first mathematical representation and each area free of holes is given the second mathematical representation, the holes and the areas free of holes in each of the first regions form a second coded aperture pattern within the respective first region, and a collection of the holes and the areas free of holes throughout the plate forms a third coded aperture pattern.

18. The apparatus of claim 17, wherein the first coded aperture pattern and at least one of the second coded aperture patterns are of a same size.

19. The apparatus of claim 17, wherein the first coded aperture pattern and at least one of the second coded aperture patterns are of different sizes.

20. The apparatus of claim 17, wherein at least two of the second coded aperture patterns are different.

* * * * *